US009134231B2

(12) United States Patent
Wang

(10) Patent No.: US 9,134,231 B2
(45) Date of Patent: Sep. 15, 2015

(54) OPTICAL MEASUREMENTS OF PROPERTIES IN SUBSTANCES USING PROPAGATION MODES OF LIGHT

(71) Applicant: Tomophase, Inc., Burlington, MA (US)

(72) Inventor: Feiling Wang, Medford, MA (US)

(73) Assignee: TOMOPHASE, INC., Burlington ( * ) Notice: Subject to any disclaimer, the term of this patent is extended or adjusted under 35 U.S.C. 154(b) by 0 days.

(21) Appl. No.: 14/049,196

(22) Filed: Oct. 8, 2013

(65) Prior Publication Data

US 2015/0098082 A1    Apr. 9, 2015

Related U.S. Application Data

(63) Continuation of application No. 13/481,733, filed on May 25, 2012, now abandoned, which is a continuation of application No. 13/195,823, filed on Aug. 1, 2011, now abandoned, which is a continuation of application No. 12/947,823, filed on Nov. 16, 2010, now abandoned, which is a continuation of application No. 12/572,889, filed on Oct. 2, 2009, now abandoned, which is a continuation of application No. 12/323,396, filed on Nov. 25, 2008, now abandoned, which is a continuation of application No. 11/842,913, filed on Aug. 21, 2007, now Pat. No. 7,456,965, which is a continuation of application No. 11/200,498, filed on Aug. 8, 2005, now Pat. No. 7,259,851, which is a continuation of application No. 10/860,094, filed on Jun. 3, 2004, now Pat. No. 6,943,881.

(60) Provisional application No. 60/475,673, filed on Jun. 4, 2003, provisional application No. 60/514,768, filed on Oct. 27, 2003, provisional application No. 60/526,935, filed on Dec. 4, 2003, provisional application No. 60/561,588, filed on Apr. 12, 2004.

(51) Int. Cl.
*G01J 3/00* (2006.01)
*G01N 21/55* (2014.01)
*G01N 21/27* (2006.01)

(52) U.S. Cl.
CPC ............... *G01N 21/55* (2013.01); *G01N 21/27* (2013.01)

(58) Field of Classification Search
CPC ............... G01J 3/02; G01J 3/28; G01J 3/42; G01N 21/31; G01N 21/552
USPC ........................................ 356/300, 445, 369
See application file for complete search history.

(56) References Cited

U.S. PATENT DOCUMENTS

| | | | | |
|---|---|---|---|---|
| 5,706,094 A * | 1/1998 | Maris | ............................. | 356/432 |
| 7,126,693 B2 * | 10/2006 | Everett et al. | ................. | 356/479 |
| 7,177,491 B2 * | 2/2007 | Dave et al. | ....................... | 385/11 |
| 7,420,685 B1 * | 9/2008 | Guo | ............................... | 356/445 |
| 2002/0093655 A1 * | 7/2002 | Everett et al. | ................. | 356/369 |
| 2004/0246490 A1 * | 12/2004 | Wang | ............................. | 356/479 |
| 2007/0158571 A1 * | 7/2007 | Cole et al. | ................. | 250/341.8 |

* cited by examiner

Primary Examiner — Abdullahi Nur

(57) ABSTRACT

This application describes designs, implementations, and techniques for controlling propagation mode or modes of light in a common optical path, which may include one or more waveguides, to sense a sample.

20 Claims, 23 Drawing Sheets

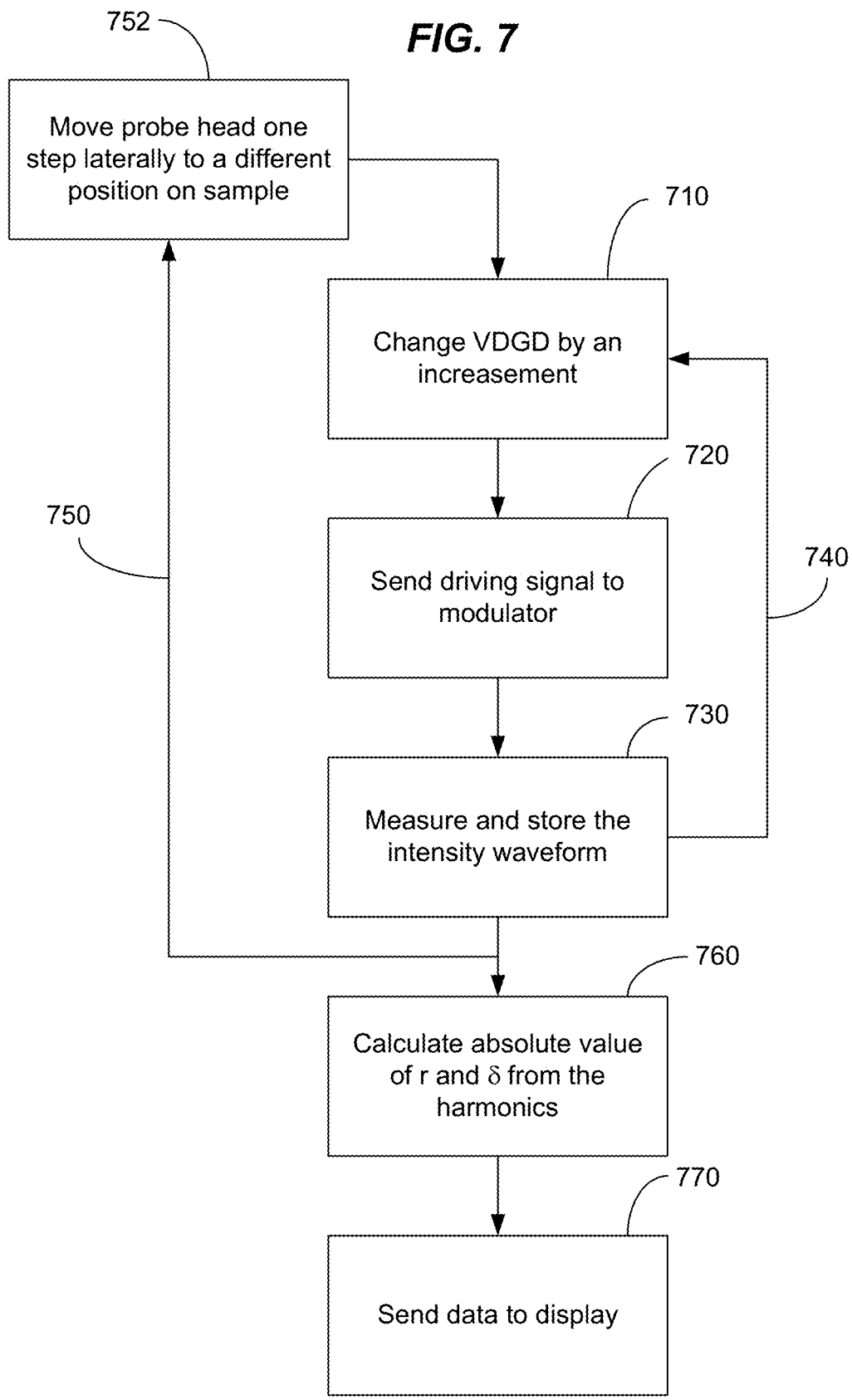

OPTICAL MEASUREMENTS OF PROPERTIES IN SUBSTANCES USING PROPAGATION MODES OF LIGHT

This patent document is a continuation application of U.S. patent application Ser. No. 13/481,733, filed May 25, 2012; which is a continuation application of U.S. patent application Ser. No. 13/195,823, filed Aug. 1, 2011; which is a continuation application of U.S. patent application Ser. No. 12/947,823, filed Nov. 16, 2010; which is a continuation application of U.S. patent application Ser. No. 12/572,889, filed Oct. 2, 2009; which is a continuation application of U.S. patent application Ser. No. 12/323,396, filed Nov. 25, 2008; which is a continuation of U.S. patent application Ser. No. 11/842,913, filed Aug. 21, 2007, now U.S. Pat. No. 7,456,965; which is a continuation application of U.S. patent application Ser. No. 11/200,498, filed Aug. 8, 2005, now U.S. Pat. No. 7,259,851; which is a continuation application of U.S. patent application Ser. No. 10/860,094, filed Jun. 3, 2004, now U.S. Pat. No. 6,943,881; which claims the benefit of the following four U.S. Provisional Applications:
1. Ser. No. 60/475,673 entitled "Method and Apparatus for Acquiring Images of Optical Inhomogeneity in Substances" and filed Jun. 4, 2003;
2. Ser. No. 60/514,768 entitled "Coherence-Gated Optical Glucose Monitor" and filed Oct. 27, 2003;
3. Ser. No. 60/526,935 entitled "Method and Apparatus for Acquiring Images of Optical Inhomogeneity in Substances" and filed Dec. 4, 2003; and
4. Ser. No. 60/561,588 entitled "Acquiring Information of Optical Inhomogeneity and Other Properties in Substances" and filed Apr. 12, 2004.

The entire disclosures of the above-referenced applications are incorporated herein by reference as part of this application.

BACKGROUND

This application relates to non-invasive, optical probing of various substances, including but not limited to, skins, body tissues and organs of humans and animals.

Investigation of substances by non-invasive and optical means has been the object of many studies as inhomogeneity of light-matter interactions in substances can reveal their structural, compositional, physiological and biological information. Various devices and techniques based on optical coherence domain reflectometry (OCDR) may be used for non-invasive optical probing of various substances, including but not limited to skins, body tissues and organs of humans and animals, to provide tomographic measurements of these substances.

In many OCDR systems, the light from a light source is split into a sampling beam and a reference beam which propagate in two separate optical paths, respectively. The light source may be partially coherent source. The sampling beam is directed along its own optical path to impinge on the substances under study, or sample, while the reference beam is directed in a separate path towards a reference surface. The beams reflected from the sample and from the reference surface are then brought to overlap with each other to optically interfere. Because of the wavelength-dependent phase delay the interference results in no observable interference fringes unless the two optical path lengths of the sampling and reference beams are very similar. This provides a physical mechanism for ranging. A beam splitter may be used to split the light from the light source and to combine the reflected sampling beam and the reflected reference beam for detection at an optical detector. This use of the same device for both splitting and recombining the radiation is essentially based on the well-known Michelson interferometer. The discoveries and the theories of the interference of partially coherent light are summarized by Born and Wolf in "Principles of Optics", Pergamon Press (1980).

Low-coherence light in free-space Michelson interferometers were utilized for measurement purposes. Optical interferometers based on fiber-optic components were used in various instruments that use low-coherence light as means of characterizing substances. Various embodiments of the fiber-optic OCDR exist such as devices disclosed by Sorin et al in U.S. Pat. No. 5,202,745, by Marcus et al in U.S. Pat. No. 5,659,392, by Mandella et al in U.S. Pat. No. 6,252,666, and by Tearney et al in U.S. Pat. No. 6,421,164. The application of OCDR in medical diagnoses in certain optical configurations has come to known as "optical coherence tomography" (OCT).

FIG. 1 illustrates a typical optical layout used in many fiber-optic OCDR systems described in the U.S. Pat. No. 6,421,164 and other publications. A fiber splitter is engaged to two optical fibers that respectively guide the sampling and reference beams in a Michelson configuration. Common to many of these and other implementations, the optical radiation from the low-coherence source is first physically separated into two separate beams where the sampling beam travels in a sample waveguide to interact with the sample while the reference beam travels in a reference waveguide. The fiber splitter than combines the reflected radiation from the sample and the reference light from the reference waveguide to cause interference.

SUMMARY

The designs, techniques and exemplary implementations for non-invasive optical probing described in this application use the superposition and interplay of different optical waves and modes propagating along substantially the same optical path inside one or more common optical waveguides. When one of the optical waves or modes interacts with the substance under study its superposition with another wave or mode can be used for the purpose of acquiring information about the optical properties of the substance.

The methods and apparatus described in this application are at least in part based on the recognition of various technical issues and practical considerations in implementing OCDR in commercially practical and user friendly apparatus, and various technical limitations in OCDR systems disclosed by the above referenced patents and other publications. As an example, at least one of disadvantages associated to the OCDR system designs shown in FIG. 1 or described in the aforementioned patents is the separation of the reference light beam from the sample light beam. Due to the separation of the optical paths, the relative optical phase or differential delay between the two beams may experience uncontrolled fluctuations and variations, such as different physical length, vibration, temperature, waveguide bending and so on. When the sample arm is in the form of a fiber-based catheter that is separate from the reference arm, for example, the manipulation of the fiber may cause a significant fluctuation and drift of the differential phase between the sample and reference light beams. This fluctuation and draft may adversely affect the measurements. For example, the fluctuation and drift in the differential phase between the two beams may lead to technical difficulties in phase sensitive measurements as absolute valuation of refractive indices and measurements of birefringence.

In various examples described in this application, optical radiation is not physically separated to travel different optical paths. Instead, all propagation waves and modes are guided along essentially the same optical path through one or more common optical waveguides. Such designs with the common optical path may be advantageously used to stabilize the relative phase among different radiation waves and modes in the presence of environmental fluctuations in the system such as variations in temperatures, physical movements of the system especially of the waveguides, and vibrations and acoustic impacts to the waveguides and system. In this and other aspects, the present systems are designed to do away with the two-beam-path configurations in various interferometer-based systems in which sample light and reference light travel in different optical paths in part to significantly reduce the above fluctuation and drift in the differential phase delay. Therefore, the present systems have a "built-in" stability of the differential optical path by virtue of their optical designs and are beneficial for some phase-sensitive measurement, such as the determination of the absolute reflection phase and birefringence. In addition, the techniques and devices described in this application simplify the structures and the optical configurations of devices for optical probing by using the common optical path to guide light.

In various applications, it may be beneficial to acquire the absorption characteristics of the material in an isolated volume inside the sample. In other case it may be desirable to map the distribution of some substances identifiable through their characteristic spectral absorbance. In some OCDR systems such as systems in aforementioned patents, it may be difficult to perform direct measurements of the optical inhomogeneity with regard to these and other spectral characteristics. The systems and techniques described in this application may be configured to allow for direct measurements of these and other spectral characteristics of a sample.

Exemplary implementations are described below to illustrate various features and advantages of the systems and techniques. One of such features is methods and apparatus for acquiring information regarding optical inhomogeneity in substance by a non-invasive means with the help of a low-coherence radiation. Another feature is to achieve high signal stability and high signal-to-noise ratio by eliminating the need of splitting the light radiation into a sample path and a reference path. Additional features include, for example, a platform on which phase-resolved measurements such as birefringence and absolute refractive indices can be made, capability of acquiring optical inhomogeneity with regard to the spectral absorbance, solving the problem of signal drifting and fading caused by the polarization variation in various interferometer-based optical systems, and an effective use of the source radiation with simple optical arrangements. Advantages of the systems and techniques described here include, among others, enhanced performance and apparatus reliability, simplified operation and maintenance, simplified optical layout, reduced apparatus complexity, reduced manufacturing complexity and cost.

Various exemplary methods and techniques for optically sensing samples are described. For example, one method for optically measuring a sample includes the following steps. A beam of guided light in a first propagation mode is directed to a sample. A first portion of the guided light in the first propagation mode is directed away from the sample at a location near the sample before the first portion reaches the sample. A second portion in the first propagation mode is directed to reach the sample. A reflection of the second portion from the sample is controlled to be in a second propagation mode different from the first propagation mode to produce a reflected second portion. Both the reflected first portion in the first propagation mode and the reflected second portion in the second propagation mode are then directed through a common waveguide into a detection module to extract information from the reflected second portion on the sample.

Another method for optically measuring a sample is also described. In this method, light in a first propagation mode is directed to a vicinity of a sample under measurement. A first portion of the light in the first propagation mode is then directed to propagate away from the sample at the vicinity of the sample without reaching the sample. A second portion of the light in the first propagation mode is directed to the sample to cause reflection at the sample. The reflected light from the sample is controlled to be in a second propagation mode that is independent from the first propagation mode to co-propagate with the first portion along a common optical path. The first portion in the first propagation mode and the reflected light in the second propagation mode are used to obtain information of the sample.

This application further describes exemplary implementations of devices and systems for optically measuring samples. One example of such devices includes a waveguide to receive and guide an input beam in a first propagation mode, and a probe head coupled to the waveguide to receive the input beam and to reflect a first portion of the input beam back to the waveguide in the first propagation mode and direct a second portion of the input beam to a sample. This probe head collects reflection of the second portion from the sample and exports to the waveguide the reflection as a reflected second portion in a second propagation mode different from the first propagation mode. This device further includes a detection module to receive the reflected first portion and the reflected second portion in the waveguide and to extract information of the sample carried by the reflected second portion.

In another example, an apparatus for optically measuring a sample is disclosed to include a light source, a waveguide supporting at least a first and a second independent propagation modes and guiding the light radiation from the light source in the first propagation mode to the vicinity of a sample under examination, a probe head that terminates the waveguide in the vicinity of the sample and reverses the propagation direction of a portion of the first propagation mode in the waveguide while transmitting the remainder of the light radiation to the sample, the probe head operable to convert reflected light from the sample into the second propagation mode, and a differential delay modulator that transmits the light in both the first and the second propagation modes from the probe head and the waveguide and varies the relative optical path length between the first and the second propagation modes. In this apparatus, a mode combiner is included to receive light from the differential delay modulator and operable to superpose the first and the second propagation modes by converting a portion of each mode to a pair of new modes. At least one photodetector is used in this apparatus to receive light in at least one of the two new modes. Furthermore, an electronic controller is used in communication with the photodetector and is operable to extract information of the sample from the output of the photodetector.

In yet another example, a device is described to include an optical waveguide, an optical probe head and an optical detection module. The optical waveguide is to guide an optical radiation in a first optical mode. The optical probe head is coupled to the optical waveguide to receive the optical radiation. The optical probe head is operable to (1) redirect a portion of the optical radiation back to the optical waveguide while transmitting the remaining radiation to a sample, (2) receive and direct the reflected or backscattered radiation from the sample into the waveguide, and (3) control the reflected or the backscattered light from the sample to be in a second optical mode different from the first optical mode. The optical detection module is used to receive the radiation redirected by the probe head through the waveguide and to convert optical radiation in the first and second optical modes, at least in part, into a common optical mode.

A further example for a device for optically measuring a sample includes an input waveguide, an output waveguide and a probe head. The input waveguide supports a first and a second different propagation modes and is used to receive and guide an input beam in the first propagation mode. The output waveguide supports a first and a second different propagation modes. The probe head is coupled to the input waveguide to receive the input beam and to the output waveguide to export light. The probe head is operable to direct a first portion of the input beam in the first propagation mode into the output waveguide and direct a second portion of the input beam to a sample. In addition, the probe head collects reflection of the second portion from the sample and exports to the output waveguide the reflection as a reflected second portion in the second propagation mode. Furthermore, this device includes a detection module to receive the reflected first portion and the reflected second portion in the output waveguide and to extract information of the sample carried by the reflected second portion.

This application also describes an example of an apparatus for optically measuring a sample. In this example, a first waveguide capable of maintaining at least one propagation mode is used. A light source that emits radiation is used to excite the propagation mode in the first waveguide. A light director is used to terminate the first waveguide with its first port, to pass the light mode entering the first port, at least in part, through a second port, and to pass the light modes entering the second port, at least in part, through a third port. The apparatus also includes a second waveguide that supports at least two independent propagation modes and having a first end coupled to the second port and a second end. Notably, a probe head is coupled to the second end of the second waveguide and operable to reverse the propagation direction of the light in part back to the second waveguide and to transmit the remainder to the sample. This probe head is operable to transform the collected light from the sample reflection to an orthogonal mode supported by the second waveguide and direct light in the orthogonal mode into the second waveguide. A third waveguide is also included which supports at least two independent propagation modes and is connected to the third port of the light director to receive light therefrom. A differential delay modulator is used to connect to the third waveguide to receive light from the second waveguide and imposes a variable phase delay and a variable path length on one mode in reference to the other. A fourth waveguide supporting at least two independent modes is coupled to the differential delay modulator to receive light therefrom. A detection subsystem is positioned to receive light from the fourth waveguide and to superpose the two propagation modes from the fourth waveguide to form two new modes, mutually orthogonal. This detection subsystem includes two photo-detectors respectively receiving light in the new modes.

These and other features, system configurations, associated advantages, and implementation variations are described in detail in the attached drawings, the textual description, and the claims.

BRIEF DESCRIPTION OF THE DRAWINGS

FIG. 7 shows one exemplary operation of the described system in FIG. 5B or the system in FIG. 3 for acquiring images of optical inhomogeneity.

DETAILED DESCRIPTION

Figure 1:
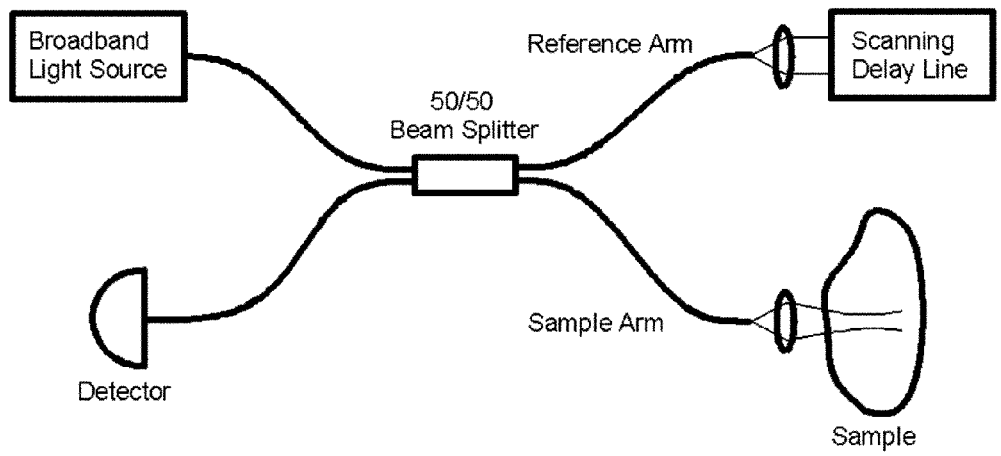
FIG. 1 shows an example of a conventional optical sensing device based on the well-known Michelson interferometer with reference and sample beams in two separate optical paths.

Energy in light traveling in an optical path such as an optical waveguide may be in different propagation modes. Different propagation modes may be in various forms. States of optical polarization of light are examples of such propagation modes. Two independent propagation modes do not mix with one another in the absence of a coupling mechanism. As an example, two orthogonally polarization modes do not interact with each other even though the two modes propagate along the same optical path or waveguide and are spatially overlap with each other. The exemplary techniques and devices described in this application use two independent propagation modes in light in the same optical path or waveguide to measure optical properties of a sample. A probe head may be used to direct the light to the sample, either in two propagation modes or in a single propagation modes, and receive the reflected or back-scattered light from the sample.

For example, one beam of guided light in a first propagation mode may be directed to a sample. A first portion of the first propagation mode may be arranged to be reflected before reaching the sample while the a second portion in the first propagation mode is allowed to reach the sample. The reflection of the second portion from the sample is controlled in a second propagation mode different from the first propagation mode to produce a reflected second portion. Both the reflected first portion in the first propagation mode and the reflected second portion in the second propagation mode are directed through a common waveguide into a detection module to extract information from the reflected second portion on the sample.

In another example, optical radiation in both a first propagation mode and a second, different propagation mode may be guided through an optical waveguide towards a sample. The radiation in the first propagation mode is directed away from the sample without reaching the sample. The radiation in the second propagation mode is directed to interact with the sample to produce returned radiation from the interaction. Both the returned radiation in the second propagation mode and the radiation in the first propagation mode are coupled into the optical waveguide away from the sample. The returned radiation in the second propagation mode and the radiation in the first propagation mode from the optical waveguide are then used to extract information of the sample.

In these and other implementations based on the disclosure of this application, two independent modes are confined to travel in the same waveguides or the same optical path in free space except for the extra distance traveled by the probing light between the probe head and the sample. This feature stabilizes the relative phase, or differential optical path, between the two modes of light, even in the presence of mechanical movement of the waveguides. This is in contrast to interferometer sensing devices in which sample light and reference light travel in different optical paths. These interferometer sensing devices with separate optical paths are prone to noise caused by the variation in the differential optical path, generally complex in optical configurations, and difficult to operate and implement. The examples described below based on waveguides are in part designed to overcome these and other limitations.

Figure 2:
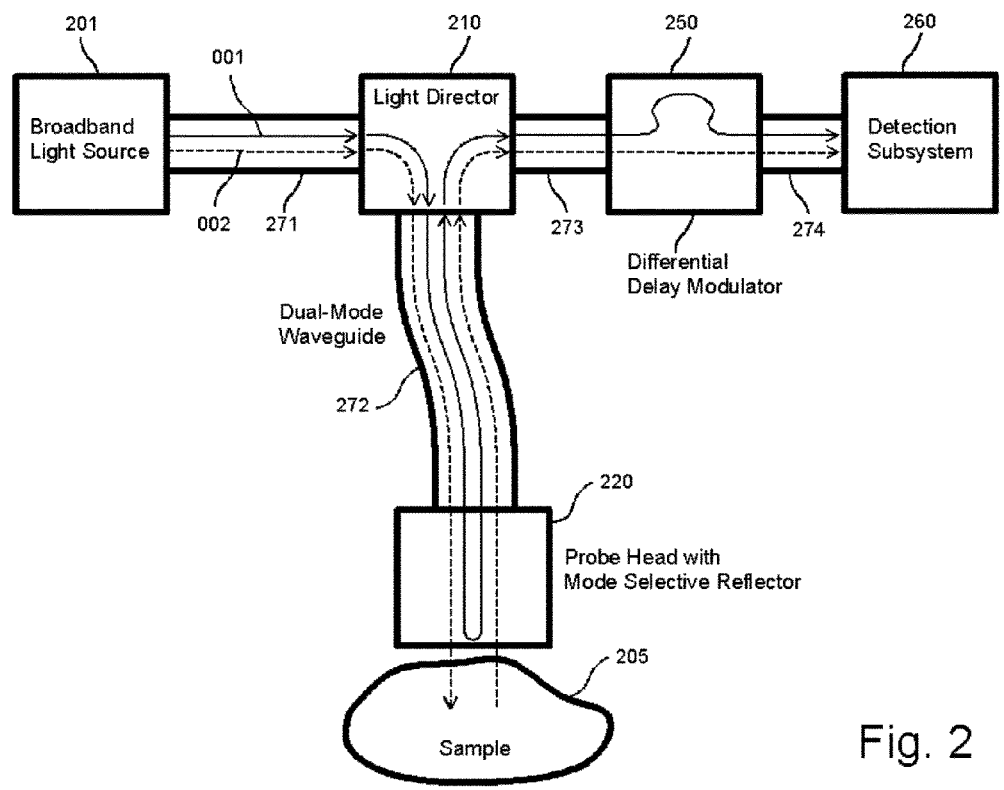
FIG. 2 shows one example of a sensing device according to one implementation.

FIG. 2 shows one example of a sensing device according to one implementation. This device directs light in two propagation modes along the same waveguide to an optical probe head near a sample 205 for acquiring information of optical inhomogeneity in the sample. A sample holder may be used to support the sample 205 in some applications. Light radiation from a broadband light source 201 is coupled into the first dual-mode waveguide 271 to excite two orthogonal propagation modes, 001 and 002. A light director 210 is used to direct the two modes to the second dual-mode waveguide 272 that is terminated by a probe head 220. The probe head 220 may be configured to perform at least the following functions. The first function of the probe head 220 is to reverse the propagation direction of a portion of light in the waveguide 272 in the mode 001; the second function of the probe head 220 is to reshape and deliver the remaining portion of the light in mode 002 to the sample 205; and the third function of the probe head 220 is to collect the light reflected from the sample 205 back to the second dual-mode waveguide 272. The back traveling light in both modes 001 and 002 is then directed by light director 210 to the third waveguide 273 and further propagates towards differential delay modulator 250. The differential delay modulator 250 is capable of varying the relative optical path length and optical phase between the two modes 001 and 002. A detection subsystem 260 is used to superpose the two propagation modes 001 and 002 to form two new modes, mutually orthogonal, to be received by photo-detectors. Each new mode is a mixture of the modes 001 and 002.

The superposition of the two modes 001 and 002 in the detection subsystem 260 allows for a range detection. The light entering the detection subsystem 260 in the mode 002 is reflected by the sample, bearing information about the optical inhomogeneity of the sample 205, while the other mode, 001, bypassing the sample 205 inside probe head 220. So long as these two modes 001 and 002 remain independent through the waveguides their superposition in the detection subsystem 260 may be used to obtain information about the sample 205 without the separate optical paths used in some conventional Michelson interferometer systems.

For the simplicity of the analysis, consider a thin slice of the source spectrum by assuming that the amplitude of the mode 001 is $E_{001}$ in a first linear polarization and that of the mode 002 is $E_{002}$ in a second, orthogonal linear polarization in the first waveguide 271. The sample 205 can be characterized by an effective reflection coefficient r that is complex in nature; the differential delay modulator 350 can be characterized by a pure phase shift $\Gamma$ exerted on the mode 001. Let us now superpose the two modes 001 and 002 by projecting them onto a pair of new modes, $E_A$ and $E_B$, by a relative 45-degree rotation in the vector space. The new modes, $E_A$ and $E_B$, may be expressed as following:

$$\begin{cases} E_A = \frac{1}{\sqrt{2}}(e^{j\Gamma}E_{001} + rE_{002}); \\ E_B = \frac{1}{\sqrt{2}}(e^{j\Gamma}E_{001} + rE_{002}). \end{cases} \quad (1)$$

It is assumed that all components in the system, except for the sample 205, are lossless. The resultant intensities of the two superposed modes are $$\begin{cases} I_A = \frac{1}{2}[E_{001}^2 + E_{002}^2 + |r|E_{001}E_{002}\cos(\Gamma - \varphi)]; \\ I_A = \frac{1}{2}[E_{001}^2 + E_{002}^2 - |r|E_{001}E_{002}\cos(\Gamma - \varphi)], \end{cases} \quad (2)$$

where $\phi$ is the phase delay associated with the reflection from the sample. A convenient way to characterize the reflection coefficient r is to measure the difference of the above two intensities, i.e.

$$I_A - I_B = |r|E_{001}E_{002}\cos(\Gamma - \phi). \quad (3)$$

If $\Gamma$ is modulated by the differential delay modulator 250, the measured signal, Eq. (3), is modulated accordingly. For either a periodic or a time-linear variation of $\Gamma$, the measured responds with a periodic oscillation and its peak-to-peak value is proportional to the absolute value of r.

For a broadband light source 201 in FIG. 2, consider the two phases, $\Gamma$ and $\phi$ to be dependent on wavelength. If the two modes 001 and 002 experience significantly different path lengths when they reach the detection system 260, the overall phase angle, $\Gamma - \phi$, should be significantly wavelength dependant as well. Consequently the measured signal, being an integration of Eq. (3) over the source spectrum, yields a smooth function even though $\Gamma$ is being varied. The condition for a significant oscillation to occur in the measured signal is when the two modes 001 and 002 experience similar path lengths at the location of their superposition. In this case the overall phase angle, $\Gamma - \phi$, becomes wavelength independent or nearly wavelength independent. In other words, for a given relative path length set by the modulator 250, an oscillation in the measured signal indicates a reflection, in the other mode, from a distance that equalizes the optical path lengths traveled by the two modes 001 and 002. Therefore the system depicted in FIG. 2 can be utilized for ranging reflection sources.

Due to the stability of the relative phase between the two modes, 001 and 002, phase-sensitive measurements can be performed with the system in FIG. 2 with relative ease. The following describes an exemplary method based on the system in FIG. 2 for the determination of the absolute phase associated with the radiation reflected from the sample 205.

In this method, a sinusoidal modulation is applied to the differential phase by the differential delay modulator 250, with a modulation magnitude of M and a modulation frequency of $\Omega$. The difference in intensity of the two new modes is the measured and can be expressed as follows:

$$I_A - I_B = |r|E_{001}E_{002}\cos[M\sin(\Omega t) - \phi]. \quad (4)$$

It is clear from Eq. (4) that the measured exhibits an oscillation at a base frequency of $\Omega$ and oscillations at harmonic frequencies of the base frequency $\Omega$. The amplitudes of the base frequency and each of the harmonics are related to $\phi$ and $|r|$. The relationships between r and the harmonics can be derived. For instance, the amplitude of the base-frequency oscillation and the second harmonic can be found from Eq. (4) to be:

$$A_\Omega = E_{001}E_{002}J_1(M)|r|\sin\phi; \quad (5a)$$

$$A_{2\Omega} = E_{001}E_{002}J_2(M)|r|\cos\phi, \quad (5b)$$

where $J_1$ and $J_2$ are Bessel functions of the first and second order, respectively. Eq. (5a) and (5b) can be used to solve for $|r|$ and $\phi$, i.e. the complete characterization of r. We can therefore completely characterize the complex reflection coefficient r by analyzing the harmonic content of various orders in the measured signal. In particular, the presence of the base-frequency component in the measured is due to the presence of $\phi$.

Figure 3:
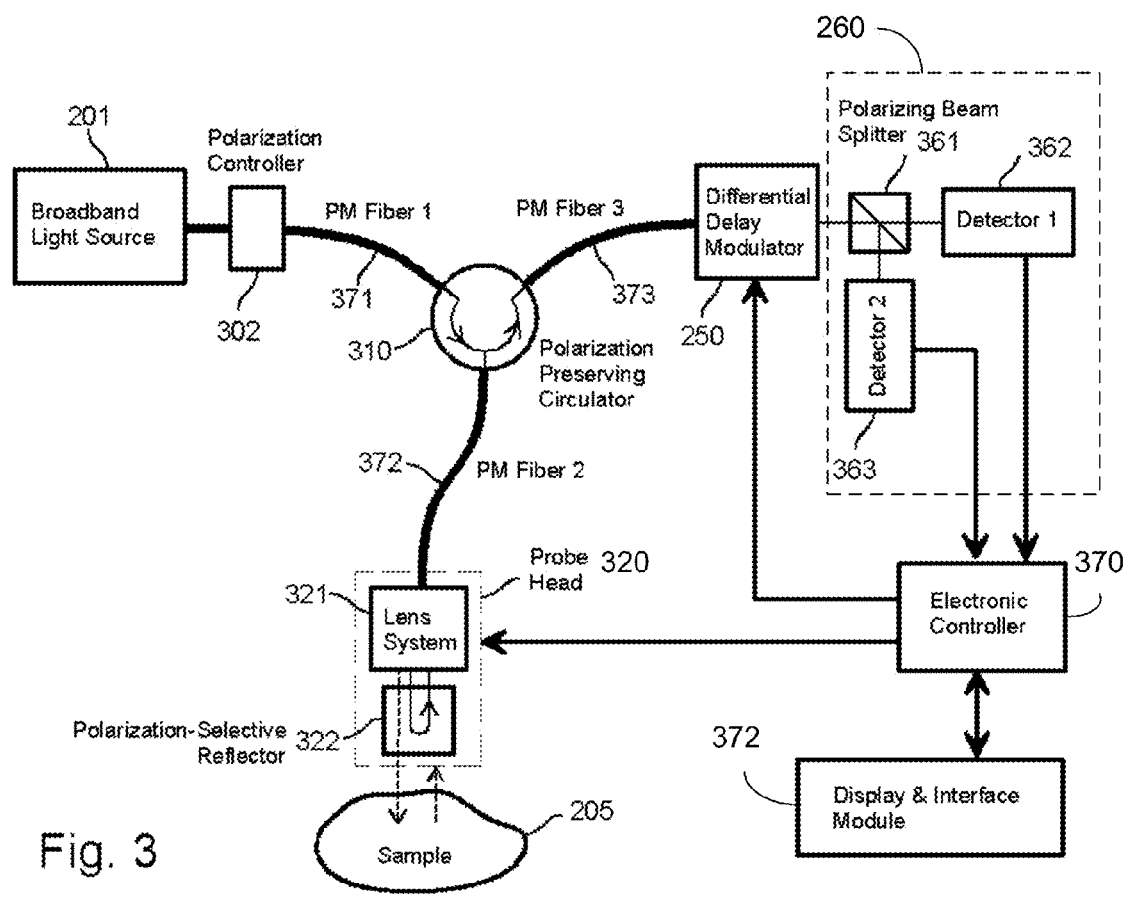
FIG. 3 shows an exemplary implementation of the system depicted in FIG. 2.

FIG. 3 shows an exemplary implementation of the system depicted in FIG. 2. The spectrum of source 201 may be chosen to satisfy the desired ranging resolution. The broader the spectrum is the better the ranging resolution. Various light sources may be used as the source 201. For example, some semiconductor superluminescent light emitting diodes (SLED) and amplified spontaneous emission (ASE) sources may possess the appropriate spectral properties for the purpose. In this particular example, a polarization controller 302 may be used to control the state of polarization in order to proportion the magnitudes of the two modes, 001 and 002, in the input waveguide 371. The waveguide 371 and other waveguides 372 and 373 may be dual-mode waveguides and are capable of supporting two independent polarization modes which are mutually orthogonal. One kind of practical and commercially available waveguide is the polarization maintaining (PM) optical fiber. A polarization maintaining fiber can carry two independent polarization modes, namely, the s-wave polarized along its slow axis and the p-wave polarized along its fast axis. In good quality polarization maintaining fibers these two modes can have virtually no energy exchange, or coupling, for substantial distances. Polarization preserving circulator 310 directs the flow of optical waves according to the following scheme: the two incoming polarization modes from fiber 371 are directed into the fiber 372; the two incoming polarization modes from fiber 372 are directed to the fiber 373. A polarization-preserving circulator 310 may be used to maintain the separation of the two independent polarization modes. For instance, the s-wave in the fiber 371 should be directed to the fiber 372 as s-wave or p-wave only. Certain commercially available polarization-preserving circulators are adequate for the purpose.

The system in FIG. 3 implements an optical probe head 320 coupled to the waveguide 372 for optically probing the sample 205. The probe head 320 delivers a portion of light received from the waveguide 372, the light in one mode (e.g., 002) of the two modes 001 and 002, to the sample 205 and collects reflected and back-scattered light in the same mode 002 from the sample 205. The returned light in the mode 002 collected from the sample 205 carries information of the sample 205 and is processed to extract the information of the sample 205. The light in the other mode 001 in the waveguide 372 propagating towards the probe head 320 is reflected back by the probe head 320. Both the returned light in the mode 002 and the reflected light in the mode 001 are directed back by the probe head 320 into the waveguide 372 and to the differential delay modulator 250 and the detection system 260 through the circulator 310 and the waveguide 373.

In the illustrated implementation, the probe head 320 includes a lens system 321 and a polarization-selective reflector (PSR) 322. The lens system 321 is to concentrate the light energy into a small area, facilitating spatially resolved studies of the sample in a lateral direction. The polarization-selective reflector 322 reflects the mode 001 back and transmits the mode 002. Hence, the light in the mode 002 transmits through the probe head 320 to impinge on the sample 205. Back reflected or scattered the light from the sample 205 is collected by the lens system 321 to propagate towards the circulator 310 along with the light in the mode 001 reflected by PSR 322 in the waveguide 372.

Figure 4:
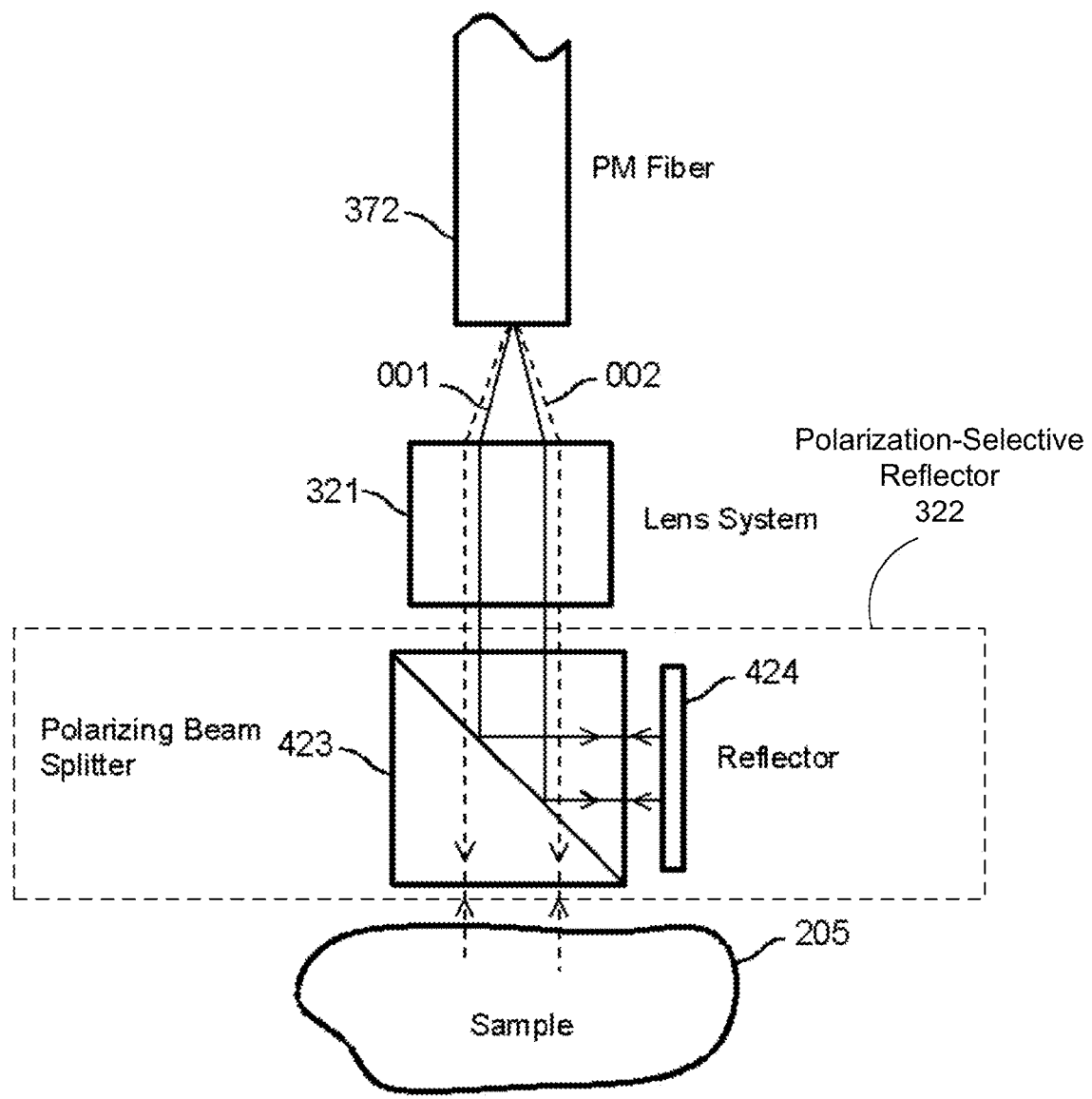
FIG. 4 shows one exemplary implementation of the probe head and one exemplary implementation of the polarization-selective reflector (PSR) used in FIG. 3.

FIG. 4 shows details of the probe head 320 and an example of the polarization-selective reflector (PSR) 322 according to one implementation. The PSR 322 includes a polarizing beam splitter (PBS) 423 and a reflector or mirror 424 in a configuration as illustrated where the PBS 423 transmits the selected mode (e.g., mode 002) to the sample 205 and reflects and diverts the other mode (e.g., mode 001) away from the sample 205 and to the reflector 424. By retro reflection of the reflector 424, the reflected mode 001 is directed back to the PBS 423 and the lens system 321. The reflector 424 may be a reflective coating on one side of beam splitter 423. The reflector 424 should be aligned to allow the reflected radiation to re-enter the polarization-maintaining fiber 372. The transmitted light in the mode 002 impinges the sample 205 and the light reflected and back scattered by the sample 205 in the mode 002 transmits through the PBS 423 to the lens system 321. The lens system 321 couples the light in both the modes 001 and 002 into the fiber 372.

In the implementation illustrated in FIG. 3, the detection system 260 includes a polarizing beam splitter 361, and two photodetectors 362 and 363. The polarizing beam splitter 361 is used to receive the two independent polarization modes 001 and 002 from the modulator 250 and superposes the two independent polarization modes 001 and 002. The beam splitter 361 may be oriented in such a way that, each independent polarization is split into two parts and, for each independent polarization mode, the two split portions possess the same amplitude. This way, a portion of the mode 001 and a portion of the mode 002 are combined and mixed in each of the two output ports of the beam splitter 361 to form a superposed new mode and each photodetector receives a superposed mode characterized by Eq. (1). The polarizing beam splitter 361 may be oriented so that the incident plane of its reflection surface makes a 45-degree angle with one of the two independent polarization mode, 001 or 002.

The system in FIG. 3 further implements an electronic controller or control electronics 370 to receive and process the detector outputs from the photodetectors 362 and 363 and to control operations of the systems. The electronic controller 370, for example, may be used to control the probe head 320 and the differential delay modulator 250. Differential delay modulator 250, under the control of the electronics and programs, generates a form of differential phase modulation as the differential path length scans through a range that matches a range of depth inside the sample 205. The electronic controller 370 may also be programmed to record and extract the amplitude of the oscillation in the measured signal characterized by Eq. (3) at various differential path lengths generated by the modulator 250. Accordingly, a profile of reflection as a function of the depth can be obtained as a one-dimensional representation of the sample inhomogeneity at a selected location on the sample 205.

For acquiring two-dimensional images of optical inhomogeneity in the sample 205, the probe head 320 may be controlled via a position scanner such as a translation stage or a piezo-electric positioner so that the probing light scans in a lateral direction, perpendicular to the light propagation direction. For every increment of the lateral scan a profile of reflection as a function of depth can be recorded with the method described above. The collected information can then be displayed on a display and interface module 372 to form a cross-sectional image that reveals the inhomogeneity of the sample 205.

In general, a lateral scanning mechanism may be implemented in each device described in this application to change the relative lateral position of the optical probe head and the sample to obtain a 2-dimensional map of the sample. A xy-scanner, for example, may be engaged either to the optical head or to a sample holder that holds the sample to effectuate this scanning in response to a position control signal generated from the electronic controller 370.

Figure 5A:
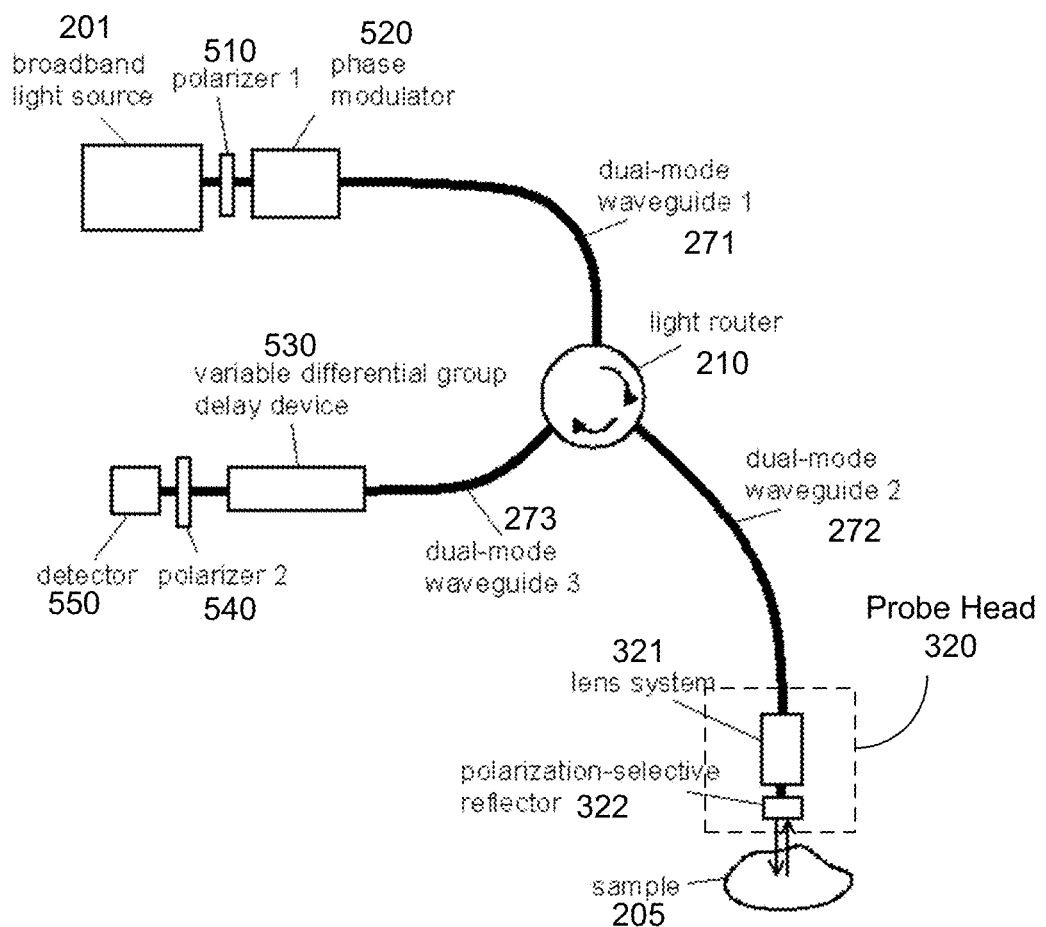
FIGS. 5A and 5B illustrate another exemplary optical sensing system that use three waveguides and a light director to direct light in two modes to and from the probe head in measuring a sample.
Figure 5B:
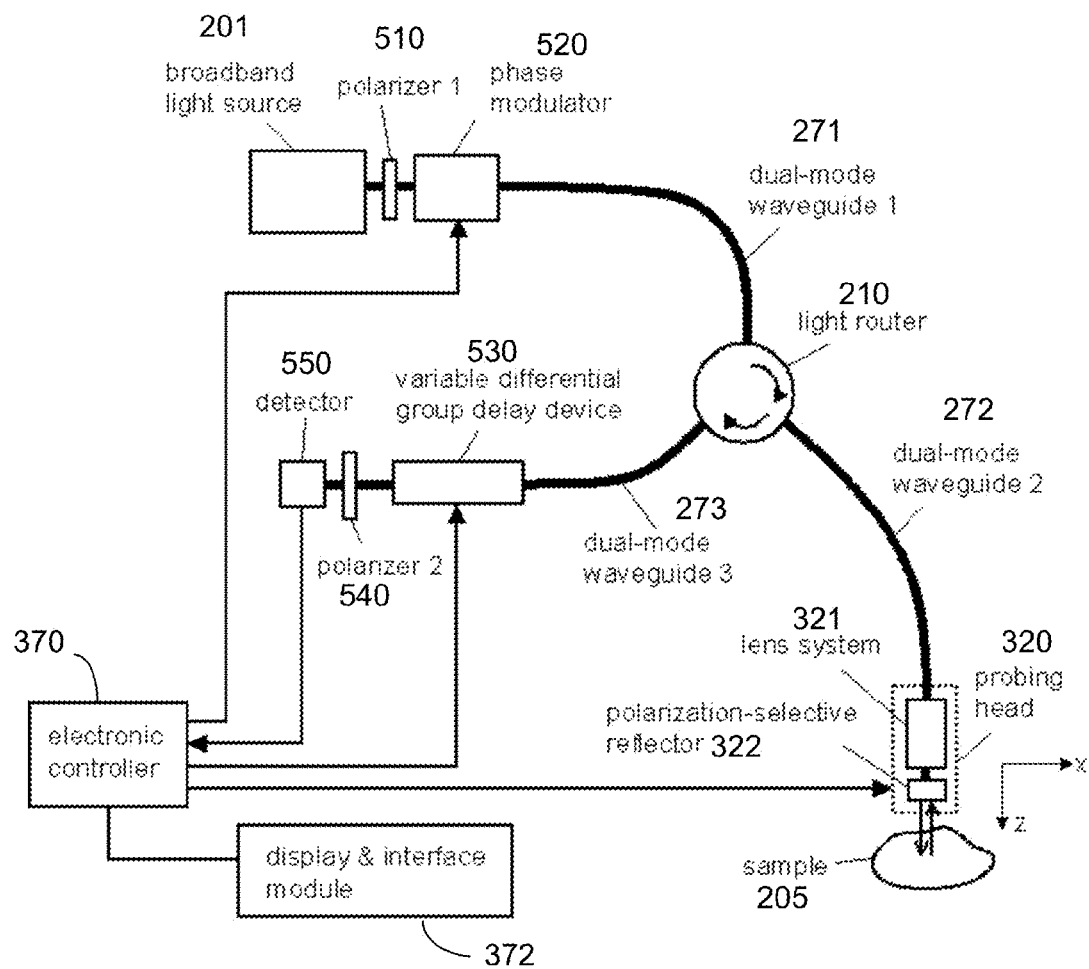

FIGS. 5A and 5B illustrate another exemplary system that use waveguides 271, 272, and 273 and a light director 210 to direct light in two modes to and from the probe head 320 in measuring the sample 205. A first optical polarizer 510 is oriented with respect to the polarization axes of the PM waveguide 271 to couple radiation from the broadband light source 201 into the waveguide 271 in two orthogonal linear polarization modes as the independent propagation modes. An optical phase modulator 520 is coupled in the waveguide 271 to modulate the optical phase of light in one guided mode relative to the other. A variable differential group delay (VDGD) device 530 is inserted in or connected to the waveguide 273 to introduce a controllable amount of optical path difference between the two waves. A second optical polarizer 540 and an optical detector 550 are used here to form a detection system. The second polarizer 540 is oriented to project both of the guided waves onto the same polarization direction so that the changes in optical path difference and the optical phase difference between the two propagation modes cause intensity variations, detectable by the detector 550.

The light from the source 201 is typically partially polarized. The polarizer 510 may be aligned so that maximum amount of light from the source 201 is transmitted and that the transmitted light is coupled to both of the guided modes in the waveguide 271 with the substantially equal amplitudes. The electric fields for the two orthogonal polarization modes S and P in the waveguide 271 can be expressed as:

$$\begin{cases} E_s = \frac{1}{\sqrt{2}}E, \\ E_p = \frac{1}{\sqrt{2}}E. \end{cases} \quad (6)$$

where the electric field transmitting the polarizer is denoted as E. It should be appreciated that the light has a finite spectral width (broadband or partially coherent). The fields can be described by the following Fourier integral:

$$E = \int E_\omega e^{j\omega t} d\omega. \quad (7)$$

For the simplicity of the analysis, a thin slice of the spectrum, i.e. a lightwave of a specific wavelength, is considered below. Without loosing generality, it is assumed that all the components, including polarizers, waveguides, Router, PSR and VDGD, are lossless. Let us designate the reflection coefficient of the sample r, that is complex in nature. The p-wave picks up an optical phase, Γ, relative to the s-wave as they reach the second polarizer 540:

$$\begin{cases} E_s = \frac{1}{\sqrt{2}}E, \\ E_p = \frac{1}{\sqrt{2}}rEe^{j\Gamma}. \end{cases} \quad (8)$$

The light that passes through Polarizer 540 can be expressed by $$E_a = \frac{1}{\sqrt{2}}(E_s + E_p) = \frac{1}{2}E(1 + re^{j\Gamma}). \quad (9)$$

The intensity of the light that impinges on the photodetector 550 is given by:

$$I = E_a E_a^* = \frac{1}{4}|E|^2[1 + |r|^2 + 2|r|\cos(\Gamma + \delta)]. \quad (10)$$

where phase angle δ reflects the complex nature of the reflection coefficient of the sample 205 and is defined by $$r = |r|e^{j\delta}. \quad (11)$$

Assuming the modulator 520 exerts a sinusoidal phase modulation, with magnitude M and frequency Ω, in the p-wave with respect to the s-wave, the light intensity received by the detector 550 can be expressed as follows:

$$I = \frac{1 + |r|^2}{4}|E|^2 + \frac{|r|}{2}|E|^2\cos[M\sin(\Omega t) + \varphi + \delta]. \quad (12)$$

where phase angle φ is the accumulated phase slip between the two modes, not including the periodic modulation due to the modulator 520. The VDGD 530 or a static phase shift in the modulator 520, may be used to adjust the phase difference between the two modes to eliminate φ.

The waveform of I is graphically shown in FIG. 4.

Figure 6:
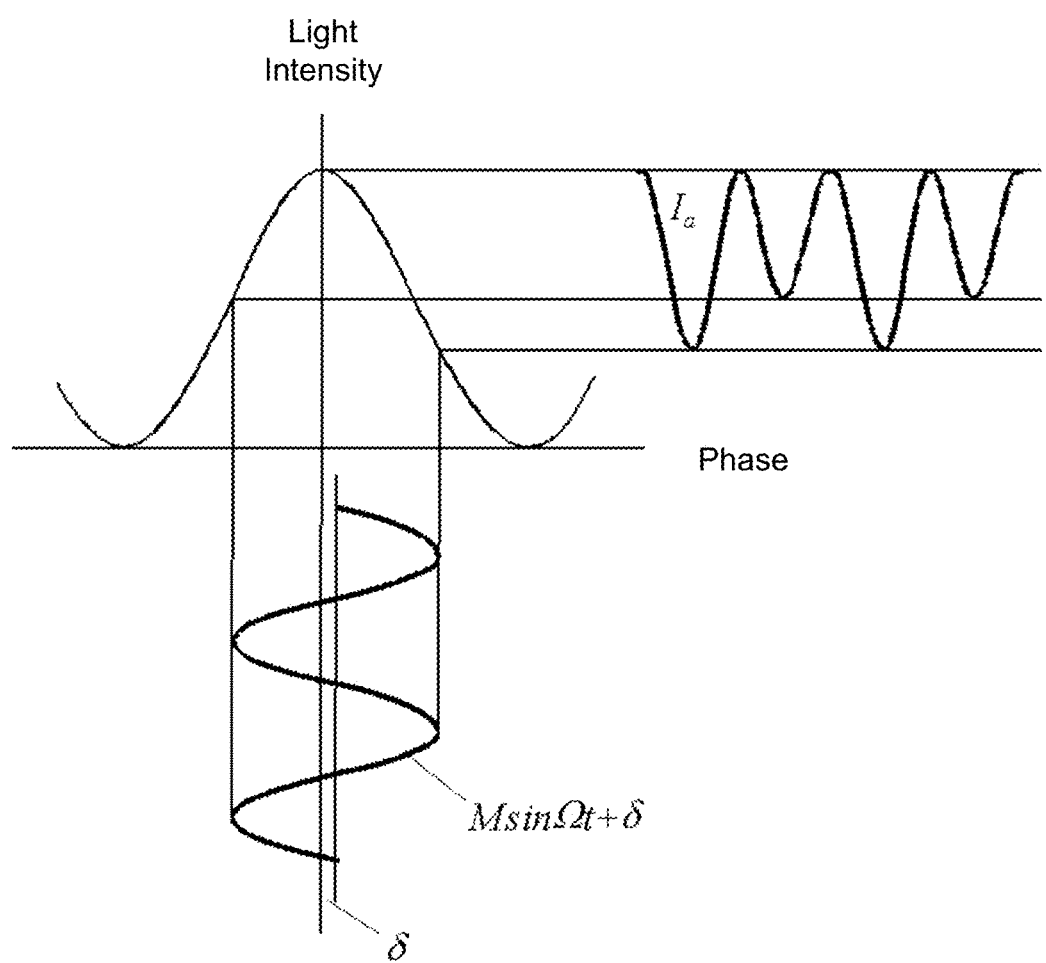
FIG. 6 illustrates the waveform of the intensity received at the detector in the system in FIGS. 5A and 5B as a function of the phase where the detected light intensity exhibits an oscillating waveform that possesses a base frequency and its harmonics.

FIG. 6 illustrates the waveform of the intensity I received at the detector 550 as a function of the phase. The detected light intensity exhibits an oscillating waveform that possesses a base frequency of Ω and its harmonics. The amplitudes of the base frequency and each of the harmonics are related to δ and |r|. The mathematical expressions for the relationships between r and the harmonics can be derived. For instance, the amplitude of the base-frequency oscillation and the second harmonic are found to be:

$$A_\Omega = 0.5|E|^2 J_1(M)|r|\sin\delta; \quad (13a)$$

$$A_{2\Omega} = 0.5|E|^2 J_2(M)|r|\cos\delta, \quad (13b)$$

where $J_1$ and $J_2$ are Bessel functions of the first and second order, respectively. Eq. (13a) and (13b) can be used to solve for |r| and δ, i.e. the complete characterization of r.

The effect of having a broadband light source 201 in the system in FIGS. 5A and 5B is analyzed below. When there is a significant differential group delay between the two propagation modes there must be an associated large phase slippage φ that is wavelength dependent. A substantial wavelength spread in the light source means that the phase slippage also possesses a substantial spread. Such a phase spread cannot be eliminated by a phase control device that does not also eliminate the differential group delay. In this case the detected light intensity is given by the following integral:

$$I = \int\left(\frac{1 + |r|^2}{4}|E(\lambda)|^2 + \frac{|r|}{2}|E(\lambda)|^2\cos[M\sin(\Omega t) + \varphi(\lambda) + \delta]\right)d\lambda. \quad (14)$$

It is easy to see that if the range of φ(λ) is comparable to π for the bandwidth of the light source no oscillation in I can be observed as oscillations for different wavelengths cancel out because of their phase difference. This phenomenon is in close analogy to the interference of white light wherein color fringes are visible only when the path difference is small (the film is thin). The above analysis demonstrates that the use of a broadband light source enables range detection using the proposed apparatus. In order to do so, let the s-wave to have a longer optical path in the system compared to the p-wave (not including its round-trip between Probing Head and Sample).

For any given path length difference in the system there is a matching distance between Probing Head and Sample, z, that cancels out the path length difference. If an oscillation in I is observed the p-wave must be reflected from this specific distance z. By varying the path length difference in the system and record the oscillation waveforms we can therefore acquire the reflection coefficient r as a function of the longitudinal distance z, or depth. By moving Probing Head laterally, we can also record the variation of r in the lateral directions.

FIG. 7 further shows one exemplary operation of the described system in FIG. 5B or the system in FIG. 3 for acquiring images of optical inhomogeneity. At step 710, the relative phase delay between the two modes is changed, e.g., increased by an increment, to a fixed value for measuring the sample 205 at a corresponding depth. This may be accomplished in FIG. 5B by using the differential delay device 530 or the bias in the differential delay modulator 250 in FIG. 3. At step 720, a modulation driving signal is sent to the modulator 520 in FIG. 5B or the modulator 250 in FIG. 3 to modulate the relative phase delay between the two modes around the fixed value. At step 730, the intensity waveform received in the detector 550 in FIG. 5B or the intensity waveforms received in the detectors 362,363 in FIG. 3 are measured and stored in the electronic controller 370. Upon completion of the step 730, the electronic controller 370 controls the differential delay device 530 in FIG. 5B or the bias in the differential delay modulator 250 in FIG. 3 to change the relative phase delay between the two modes to a different fixed value for measuring the sample 205 at a different depth. This process iterates as indicated by the processing loop 740 until desired measurements of the sample at different depths at the same location are completed. At this point, electronic controller 370 controls the probe head 320 to laterally move to a new location on the sample 205 and repeat the above measurements again until all desired locations on the sample 205 are completed. This operation is represented by the processing loop 750. The electronic controller 370 processes each measurement to compute the values of δ and |r| from the base oscillation and the harmonics at step 760. Such data processing may be performed after each measurement or after all measurements are completed. At step 770, the computed data is sent to the display module 372.

In the above implementations, light for sensing the sample 205 is not separated into two parts that travel along two different optical paths. Two independent propagation modes of the light are guided essentially in the same waveguide at every location along the optical path except for the extra distance traveled by one mode between the probe head 320 and the sample 205. After redirected by the probe head 320, the two modes are continuously guided in the same waveguide at every location along the optical path to the detection module.

Alternatively, the light from the light source to the probe head may be controlled in a single propagation mode (e.g., a first propagation mode) rather than two different modes. The probe head may be designed to cause a first portion of the first mode to reverse its propagation direction while directing the remaining portion, or a second portion, to reach the sample. The reflection or back scattered light of the second portion from the sample is collected by the probe head and is controlled in the second propagation mode different from the first mode to produce a reflected second portion. Both the reflected first portion in the first propagation mode and the reflected second portion in the second propagation mode are directed by the probe head through a common waveguide into the detection module for processing. In comparison with the implementations that use light in two modes throughout the system, this alternative design further improves the stability of the relative phase delay between the two modes at the detection module and provides additional implementation benefits.

Figure 8A:
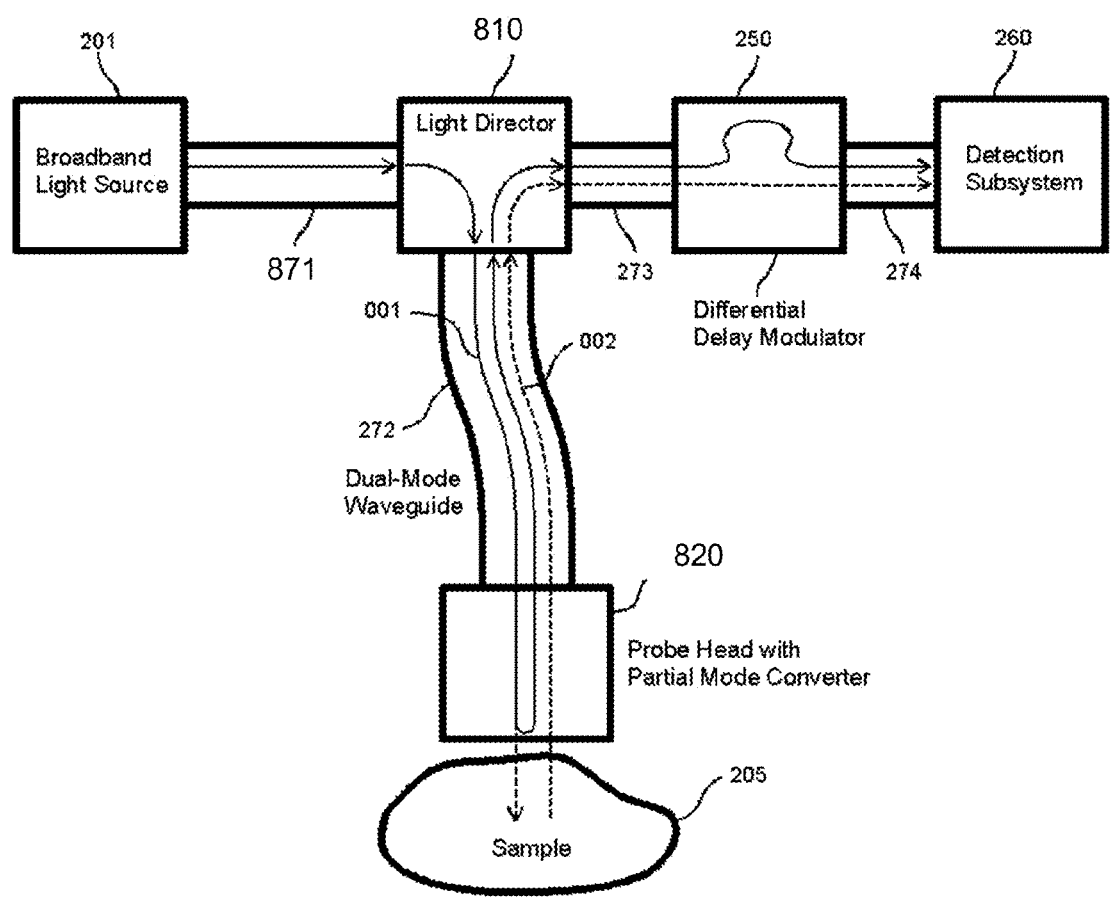
FIGS. 8A and 8B illustrate one exemplary design of the optical layout of the optical sensing system and its system implementation with an electronic controller where light in a single mode is used as the input light.
Figure 8B:
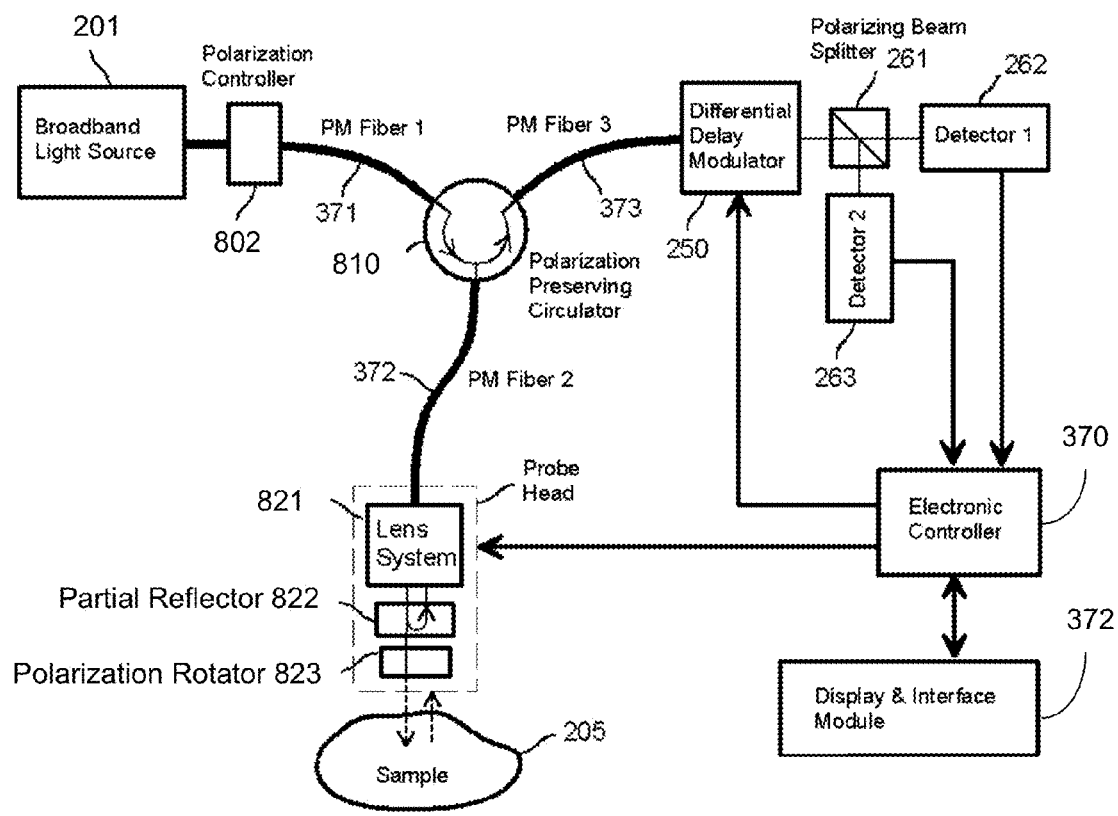

FIGS. 8A and 8B illustrate one exemplary design of the optical layout of the optical sensing system and its system implementation with an electronic controller. An input waveguide 871 is provided to direct light in a first propagation mode, e.g., the mode 001, from the broadband light source 201 to a light director 810. The waveguide 871 may be a mode maintaining waveguide designed to support at least one propagation mode such as the mode 001 or 002. When light is coupled into the waveguide 871 in a particular mode such as the mode 001, the waveguide 871 essentially maintains the light in the mode 001. A polarization maintaining fiber supporting two orthogonal linear polarization modes, for example, may be used as the waveguide 871. Similar to systems shown in FIGS. 2, 3, 5A and 5B, dual-mode waveguides 272 and 273 are used to direct the light. A light director 510 is used to couple the waveguides 871, 272, and 273, to convey the mode 001 from the input waveguide 871 to one of the two modes (e.g., modes 001 and 002) supported by the dual-mode waveguide 272, and to direct light in two modes from the waveguide 272 to the dual-mode waveguide 273. In the example illustrated in FIG. 8A, the light director 810 couples the light in the mode 001 from the waveguide 871 into the same mode 001 in the waveguide 272. Alternatively, the light director 810 may couple the light in the mode 001 from the waveguide 871 into the different mode 002 in the waveguide 272. The dual-mode waveguide 271 is terminated at the other end by a probe head 820 which couples a portion of light to the sample 205 for sensing.

The probe head 820 is designed differently from the prove head 320 in that the probe head 830 converts part of light in the mode 001 into the other different mode 002 when the light is reflected or scattered back from the sample 205. Alternatively, if the light in the waveguide 272 that is coupled from the waveguide 871 is in the mode 002, the probe head 820 converts that part of light in the mode 002 into the other different mode 001 when the light is reflected or scattered back from the sample 205. In the illustrated example, the probe head 820 performs these functions: a) to reverse the propagation direction of a small portion of the incoming radiation in mode 001; b) to reshape the remaining radiation and transmit it to the sample 205; and c) to convert the radiation reflected from the sample 205 to an independent mode 002 supported by the dual-mode waveguide 272. Since the probe head 820 only converts part of the light into the other mode supported by the waveguide 272, the probe head 820 is a partial mode converter in this regard. Due to the operations of the probe head 820, there are two modes propagating away from the probe head 820, the mode 001 that bypasses the sample 205 and the mode 002 for light that originates from sample reflection or back scattering. From this point on, the structure and operations of the rest of the system shown in FIG. 8A may be similar to the systems in FIGS. 2, 3, 5A, and 5B.

FIG. 8B shows an exemplary implementation of the design in FIG. 8A where an electronic controller 3370 is used to control the differential delay modulator 250 and the probe head 820 and a display and interface module 372 is provided. Radiation from broadband light source 201, which may be partially polarized, is further polarized and controlled by an input polarization controller 802 so that only a single polarization mode is excited in polarization-maintaining fiber 371 as the waveguide 871 in FIG. 8A. a polarization preserving circulator may be used to implement the light director 810 for routing light from the waveguide 371 to the waveguide 372 and from the waveguide 372 to the waveguide 373.

The probe head 820 in FIG. 8B may be designed to include a lens system 821 similar to the lens system 321, a partial reflector 822, and a polarization rotator 823. The partial reflector 822 is used to reflect the first portion of light received from the waveguide 372 back to the waveguide 372 without changing its propagation mode and transmits light to and from the sample 205. The polarization rotator 823 is used to control the light from the sample 205 to be in the mode 002 upon entry of the waveguide 372.

Figure 9:
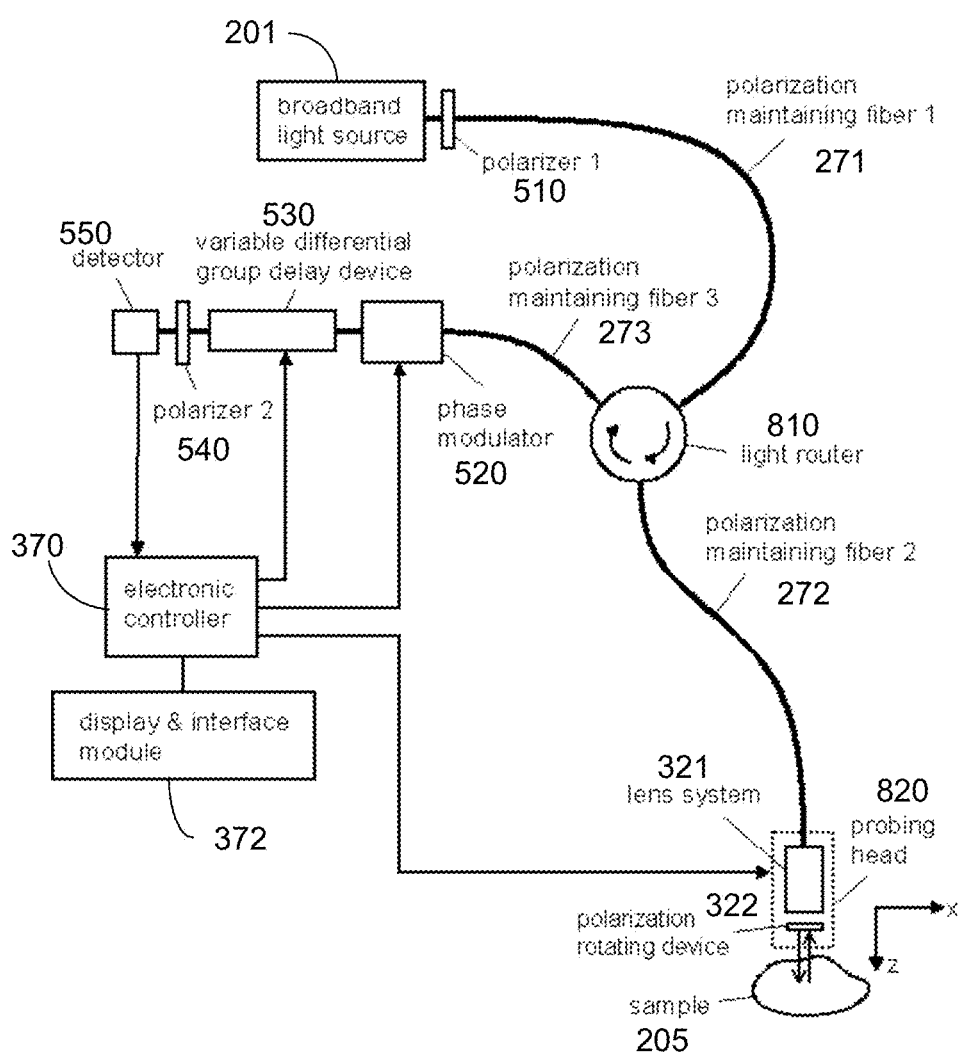
FIG. 9 shows another example of a system implementation where the optical probe head receives light in a single input mode and converts part of light into a different mode.

FIG. 9 shows another example of a system implementation where the optical probe head 820 receives light in a single input mode and converts part of light into a different mode. An input polarizer 510 is used in the input PM fiber 272 to control the input light in the single polarization mode. A phase modulator 520 and a variable differential group delay device 530 are coupled to the output PM fiver 273 to control and modulate the relative phase delay of the two modes before optical detection. An output polarizer 540 is provided to mix the two modes and the detector 550 is used to detect the output from the output polarizer 540.

Figure 10A:
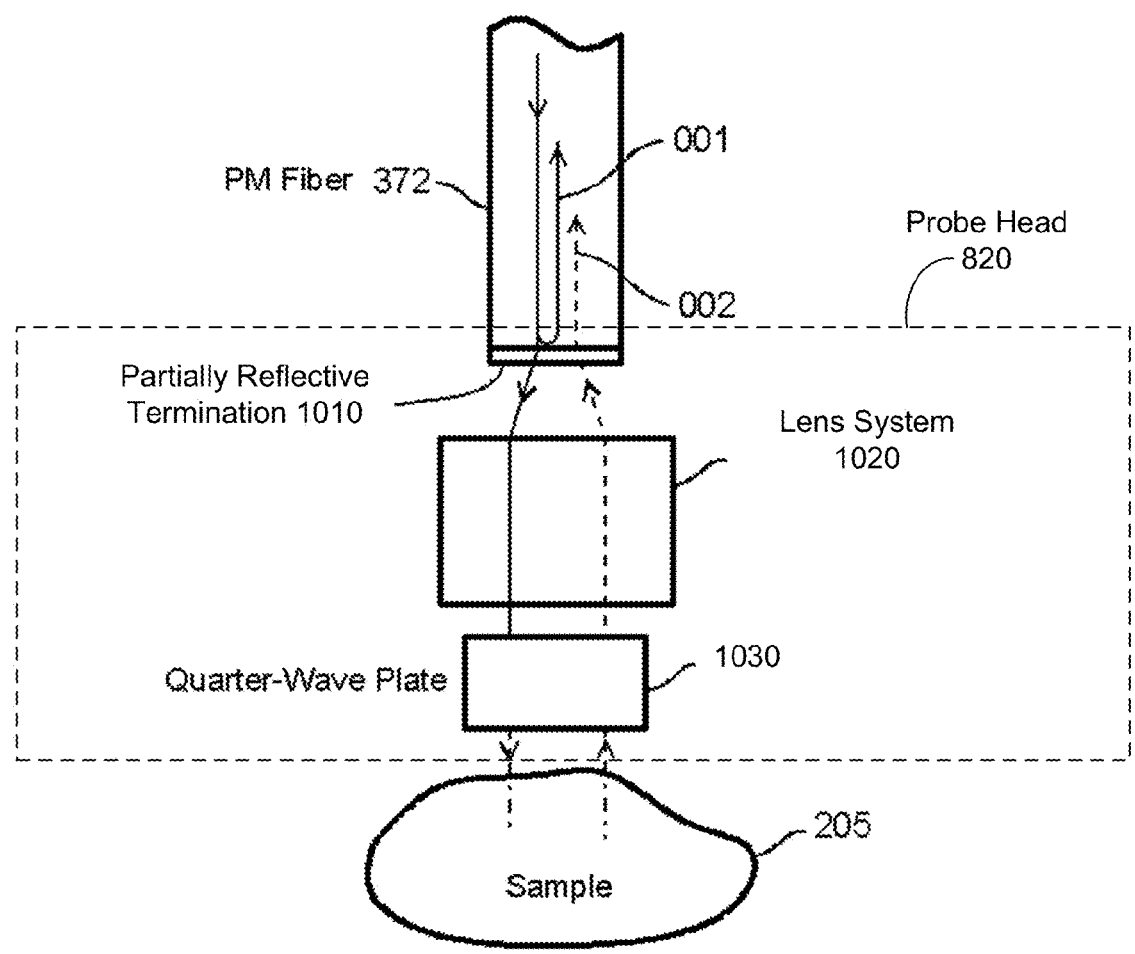
FIGS. 10A and 10B show two examples of the possible designs for the probe head used in sensing systems where the input light is in a single mode.
Figure 10B:
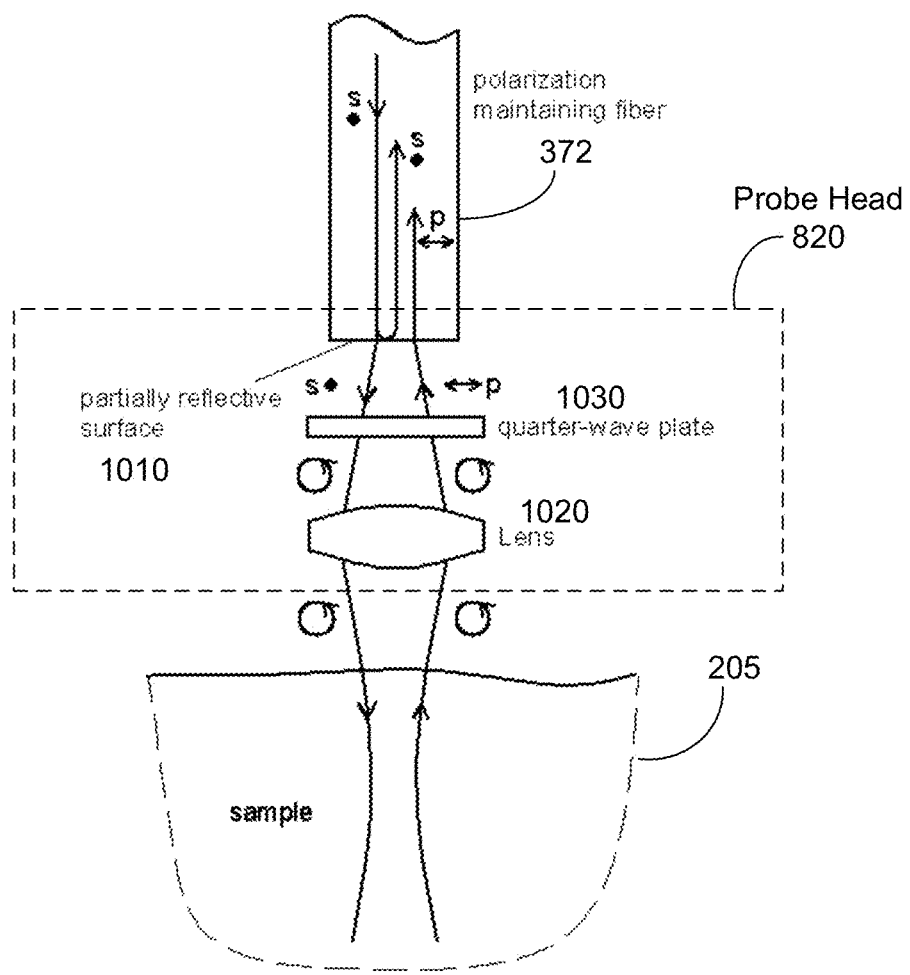

FIGS. 10A and 10B show two examples of the possible designs for the probe head 820 including a partially reflective surface 1010, a lens system 1020, and a quarter-wave plate 1030 for rotating the polarization and to convert the mode. In FIG. 10A, the termination or end facet of polarization-maintaining fiber 372 is used as the partial reflector 1010. An uncoated termination of an optical fiber reflects approximately 4% of the light energy. Coatings can be used to alter the reflectivity of the termination to a desirable value. The lens system 1020 reshapes and delivers the remaining radiation to sample 205. The other role played by the lens system 1020 is to collect the radiation reflected from the sample 205 back into the polarization-maintaining fiber 372. The quarter wave plate 1030 is oriented so that its optical axis make a 45-degree angle with the polarization direction of the transmitted light. Reflected light from the sample 205 propagates through the quarter wave plate 1030 once again to become polarized in a direction perpendicular to mode 001, i.e. mode 002. Alternatively, the quarter wave plate 1030 may be replaced by a Faraday rotator. The head design in FIG. 10B changes the positions of the lens system 1020 and the quarter wave plate or Faraday rotator 1030.

Figure 11:
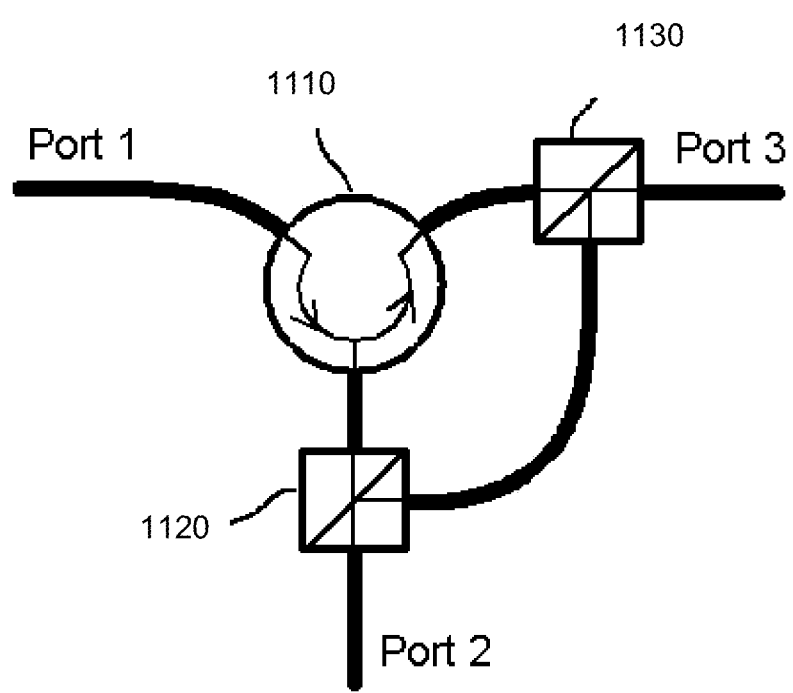
FIG. 11 shows one implementation of a light director that includes a polarization-maintaining optical circulator and two polarization beam splitters.

In the examples in FIGS. 8A, 8B, and 9, there is only one polarization mode entering the light director 810 or the polarization-preserving circulator from waveguide 871 or 371. Therefore, the light director 810 or the polarization preserving circulator may be constructed with a polarization-maintaining optical circulator 1110 and two polarization beam splitters 1120 and 1130 as shown in FIG. 11. The polarization-maintaining circulator 1110 is used to convey only one polarization mode among its three ports, rather than both modes as in the case shown in FIGS. 3, 5A and 5B. The polarizing beam splitter 1120 and 1130 are coupled to polarization-maintaining circulator 1110 so that both polarization modes entering Port 2 are conveyed to Port 3 and remain independent.

Figure 12:
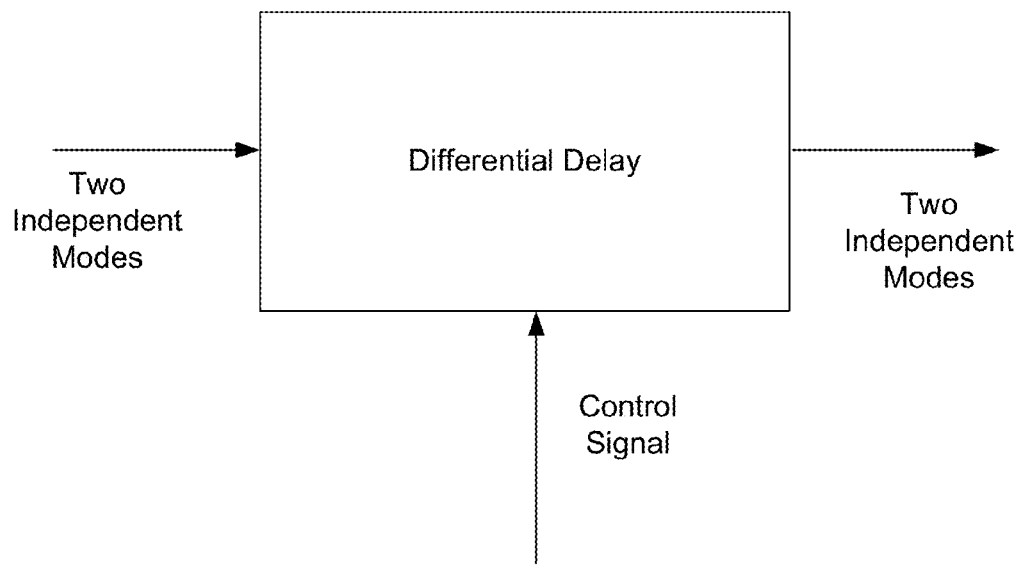
FIG. 12 illustrates an example of the optical differential delay modulator used in present optical sensing systems where an external control signal is applied to control a differential delay element to change and modulate the relative delay in the output.

A number of hardware choices are available for differential delay modulator 250. FIG. 12 illustrates the general design of the modulator 250 where an external control signal is applied to control a differential delay element to change and modulate the relative delay in the output. Either mechanical or non-mechanical elements may be used to produce the desired relative delay between the two modes and the modulation on the delay.

Figure 12A:
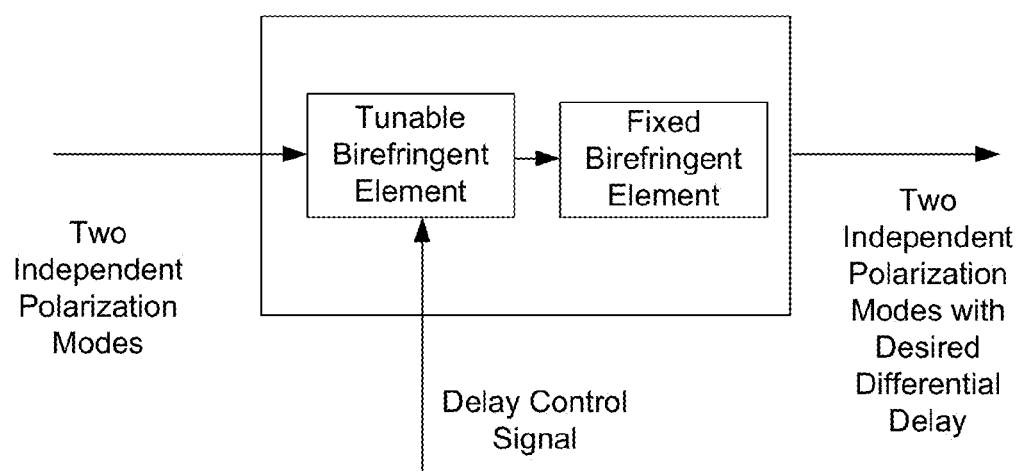
FIGS. 12A and 12B illustrate two exemplary devices for implementing the optical differential delay modulator in FIG. 12.

In one implementation, a non-mechanical design may include one or more segments of tunable birefringent materials such as liquid crystal materials or electro-optic birefringent materials such as lithium niobate crystals in conjunction with one or more fixed birefringent materials such as quartz and rutile. The fixed birefringent material provides a fixed delay between two modes and the tunable birefringent material provides the tuning and modulation functions in the relative delay between the two modes. FIG. 12A illustrates an example of this non-mechanical design where the two modes are not physically separated and are directed through the same optical path with birefringent segments which alter the relative delay between two polarization modes.

Figure 12B:
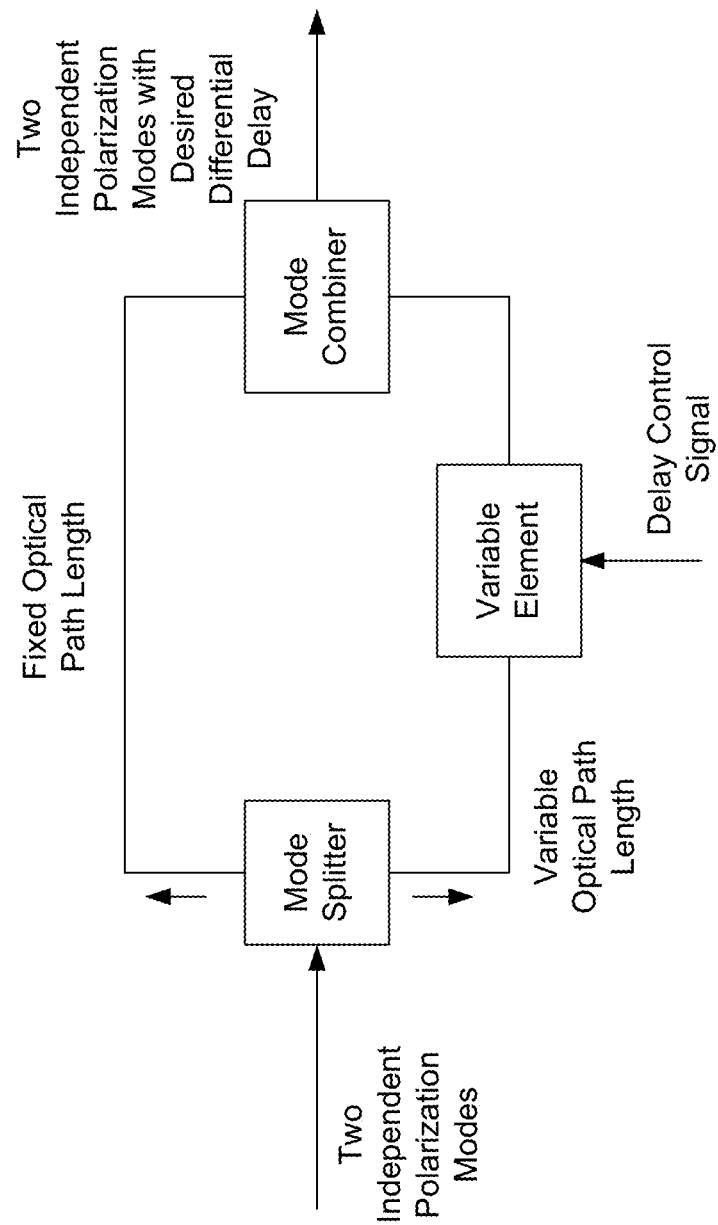

FIG. 12B shows a different design where the two modes in the received light are separated by a mode splitter into two different optical paths. A variable delay element is inserted in one optical path to adjust and modulate the relative delay in response to an external control signal. A mode combiner is then used to combine the two modes together in the output. The mode splitter and the mode combiner may be polarization beams splitters when two orthogonal linear polarizations are used as the two modes.

The variable delay element in one of the two optical paths may be implemented in various configurations. For example, the variable delay element may be a mechanical element. A mechanical implementation of the device in FIG. 12B may be constructed by first separating the radiation by polarization modes with a polarizing beam splitter, one polarization mode propagating through a fixed optical path while the other propagating through a variable optical path having a piezoelectric stretcher of polarization maintaining fibers, or a pair of collimators both facing a mechanically movable retroreflector in such a way that the light from one collimator is collected by the other through a trip to and from the retroreflector, or a pair collimators optically linked through double passing a rotatable optical plate and bouncing off a reflector.

Figure 13A:
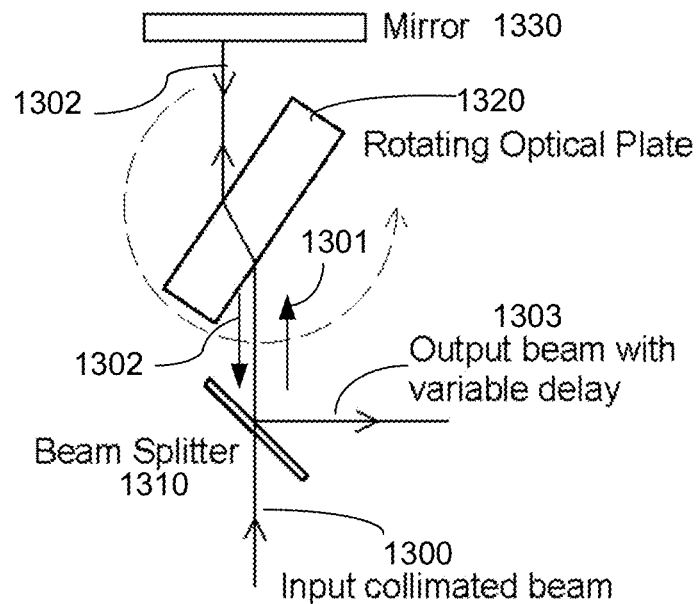
FIGS. 13A and 13B illustrate two examples of a mechanical variable delay element suitable for implementing the optical differential delay modulator shown in FIG. 12B.
Figure 13B:
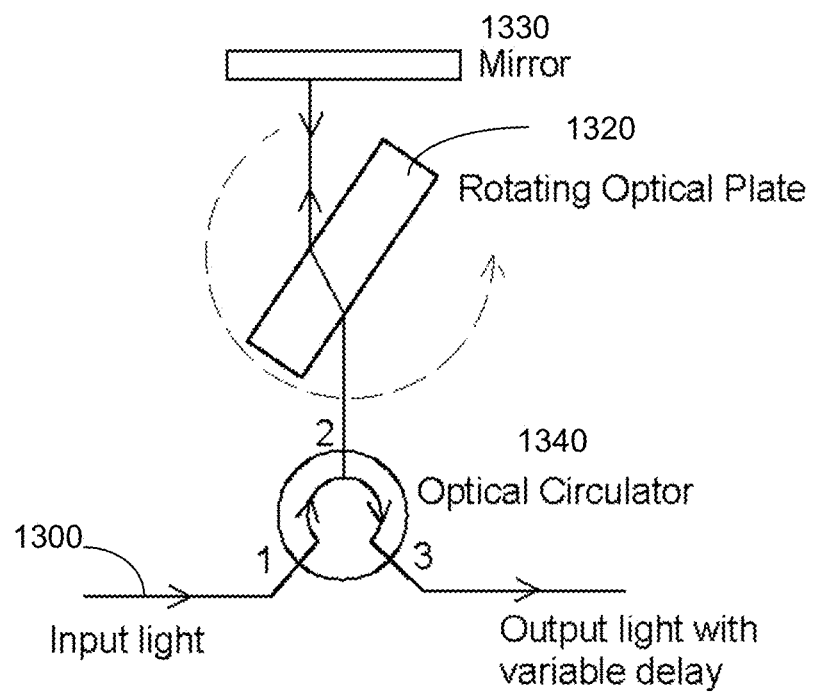

FIGS. 13A and 13B illustrate two examples of a mechanical variable delay element suitable for FIG. 12B. Such a mechanical variable delay device may be used to change the optical path length of a light beam at high speeds and may have various applications other than what is illustrated in FIG. 12B. In addition, the optical systems in this application may use such a delay device.

The mechanical delay device shown in FIG. 13A includes an optical beam splitter 1310, a rotating optical plate 1320 which may be a transparent plate, and a mirror or reflector 1330. The beam splitter 1310 is used as the input port and the output port for the device. The rotating optical plate 1320 is placed between the mirror 1330 and the beam splitter 1310. The input light beam 1300 is received by the beam splitter 1310 along the optical path directing from the beam splitter 1310 to the mirror 1330 through the rotating optical plate 1320. A portion of the light 1300 transmitting through the beam splitter 1310 is the beam 1301 which impinges on and transmits through the rotating optical plate 1320. The mirror or other optical reflector 1330 is oriented to be perpendicular to the light beam incident to the optical plate 1310 from the opposite side. The reflected light beam 1302 from the mirror 1320 traces the same optical path back traveling until it encounters the Beam Splitter 1310. The Beam Splitter 1310 deflects part of the back traveling light 1302 to a different direction as the output beam 1303.

In this device, the variation of the optical path length is caused by the rotation of the Optical Plate 1320. The Optical Plate 1320 may be made of a good quality optical material. The two optical surfaces may be flat and well polished to minimize distortion to the light beam. In addition, the two surfaces should be parallel to each other so that the light propagation directions on both sides of the Optical Plate 1320 are parallel. The thickness of the Optical Plate 1320 may be chosen according to the desirable delay variation and the range of the rotation angle. The optical path length experienced by the light beam is determined by the rotation angle of the Optical Plate 1320. When the surfaces of the Optical Plate 1320 is perpendicular to the light beam (incident angle is zero), the path length is at its minimum. The path length increases as the incident angle increases.

In FIG. 13A, it may be beneficial to collimate the input light beam so that it can travel the entire optical path without significant divergence. The Optical Plate 1320 may be mounted on a motor for periodic variation of the optical delay. A good quality mirror with a flat reflecting surface should be used to implement the mirror 1330. The reflecting surface of the mirror 1330 may be maintained to be perpendicular to the light beam.

If a linearly polarized light is used as the input beam 1300 in FIG. 13A, it is beneficial to have the polarization direction of the light parallel to the incident plane (in the plane of the paper) as less reflection occurs at the surfaces of Optical Plate 1320 for this polarization compared to other polarization directions. Antireflection coatings can be used to further reduce the light reflection on the surfaces of the Optical Plate 1320.

The beam splitter 1310 used in FIG. 13A uses both its optical transmission and optical reflection to direct light. This aspect of the beam splitter 1310 causes reflection loss in the output of the device due to the reflection loss when the input light 1300 first enters the device through transmission of the beam splitter 1310 and the transmission loss when the light exits the device through reflection of the beam splitter 1310. For example, a maximum of 25% of the total input light may be left in the output light if the beam splitter is a 50/50 beam splitter. To avoid such optical loss, an optical circulator may be used in place of the beam splitter 1320. FIG. 13B illustrates an example where the optical circulator 1340 with 3 ports is used to direct input light to the optical plate 1320 and the mirror 1330 and directs returned light to the output port. The optical circulator 1340 may be designed to direct nearly all light entering its port 1 to port 2 and nearly all light entering its port 2 to the port 3 with nominal optical loss and hence significantly reduces the optical loss in the device. Commercially available optical circulators, either free-space or fiber-based, may be used to implement the circulator 1340.

Figure 14A:
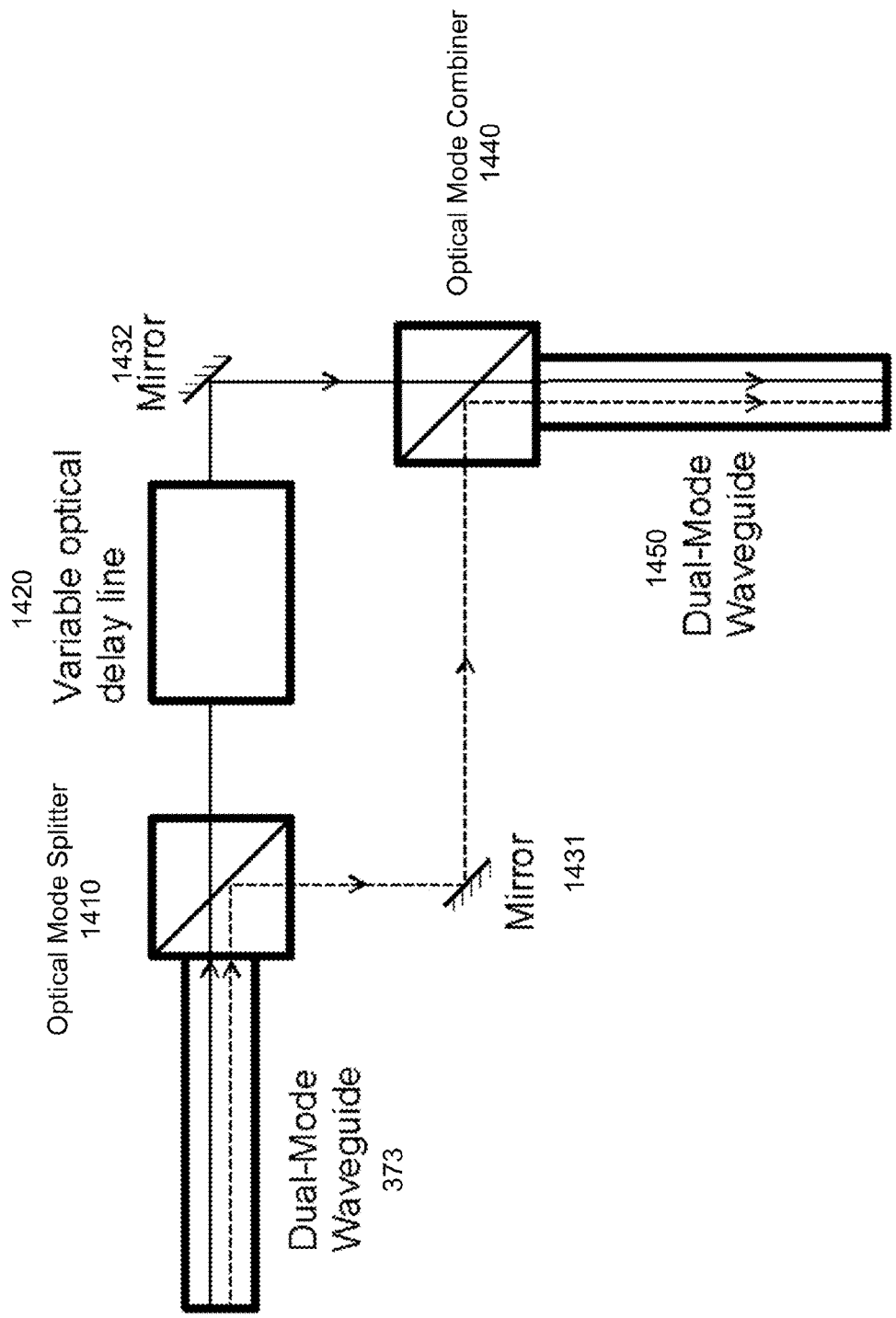
FIG. 14A shows an exemplary implementation of the delay device in FIG. 12B as part of or the entire differential delay modulator.
Figure 14B:
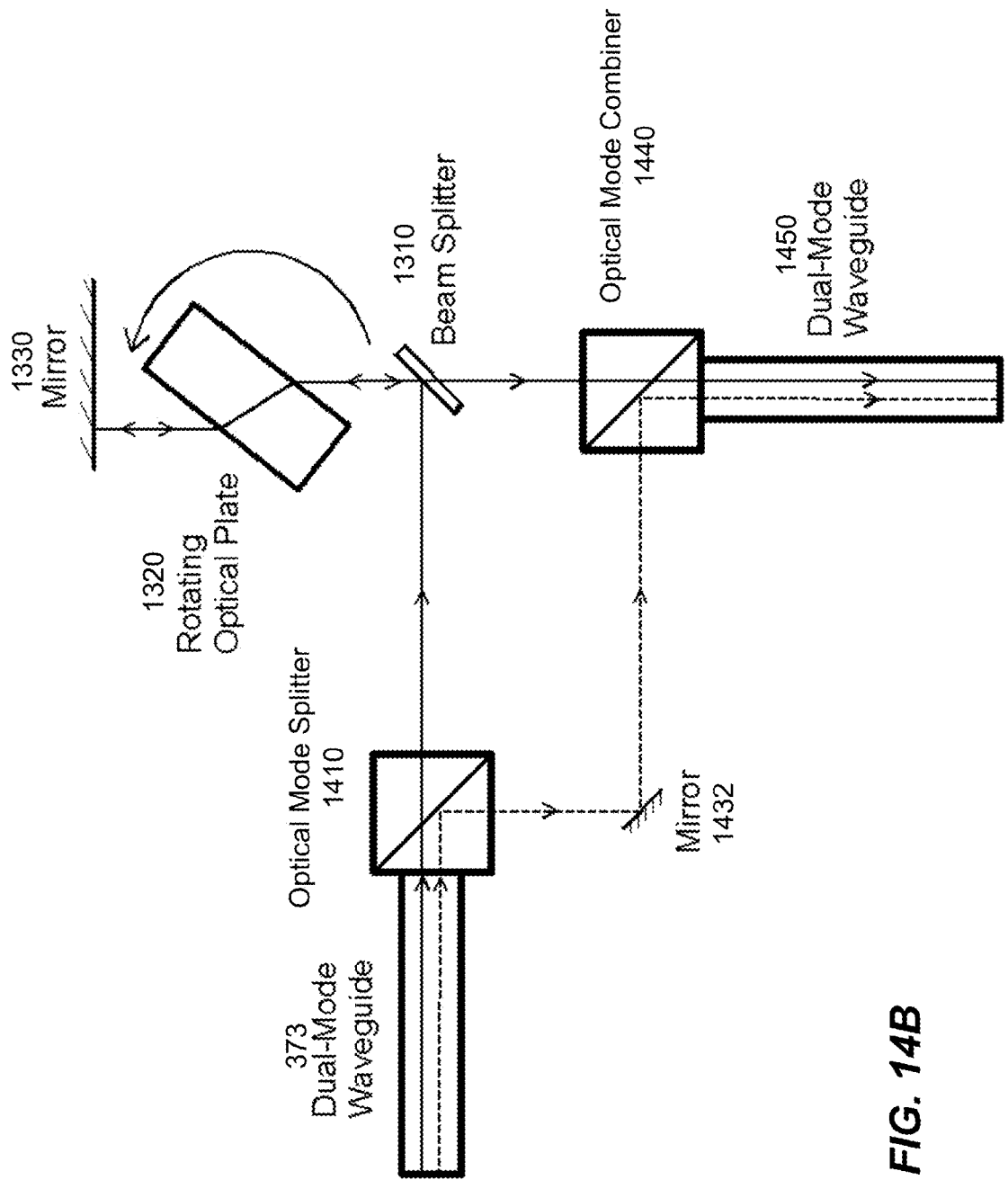
FIG. 14B shows a delay device based on the design in FIG. 14A where the mirror and the variable optical delay line are implemented by the mechanical delay device in FIG. 13A.

FIG. 14A shows an exemplary implementation of the delay device in FIG. 12B as part of or the entire differential delay modulator 250. A first optical mode splitter 1410 is used to separate two modes in the waveguide 373 into two paths having two mirrors 1431 and 1432, respectively. A second optical mode splitter 1440, which is operated as a mode combiner, is used to combine the two modes into an output. If the two modes are two orthogonal linear polarizations, for example, polarization beam splitters may be used to implement the 1410 and 1440. A variable optical delay line or device 1420 is placed in the upper path to control the differential delay between the two paths. The output may be coupled into another dual-mode waveguide 1450 leading to the detection module or directly sent into the detection module. FIG. 14B shows a delay device based on the design in FIG. 14A where the mirror 1432 and the variable optical delay line 1420 are implemented by the mechanical delay device in FIG. 13A. The mechanical delay device in FIG. 13B may also be used to implement the device in FIG. 14A.

In the above examples, a single dual-mode waveguide 272 or 372 is used as an input and output waveguide for the probe head 220, 320, or 820. Hence, the input light, either in a single mode or two independent modes, is directed into the probe head through that dual-mode waveguide 272 or 372, and the output light in the two independent modes is also directed from the probe head to the detection subsystem or detector.

Alternatively, the single dual-mode waveguide 272 or 372 may be replaced by two separate waveguides, one to direct input light from the light source to the probe head and another to direct light from the probe head to the detection subsystem or detector. As an example, the device in FIG. 2 may have a second waveguide different from the waveguide 272 to direct reflected light in two different modes from the optical probe head 220 to the modulator 250 and the detection subsystem 260. In this design, the light director 210 may be eliminated. This may be an advantage. In implementation, the optics within the probe head may be designed to direct the reflected light in two modes to the second waveguide.

Figure 15:
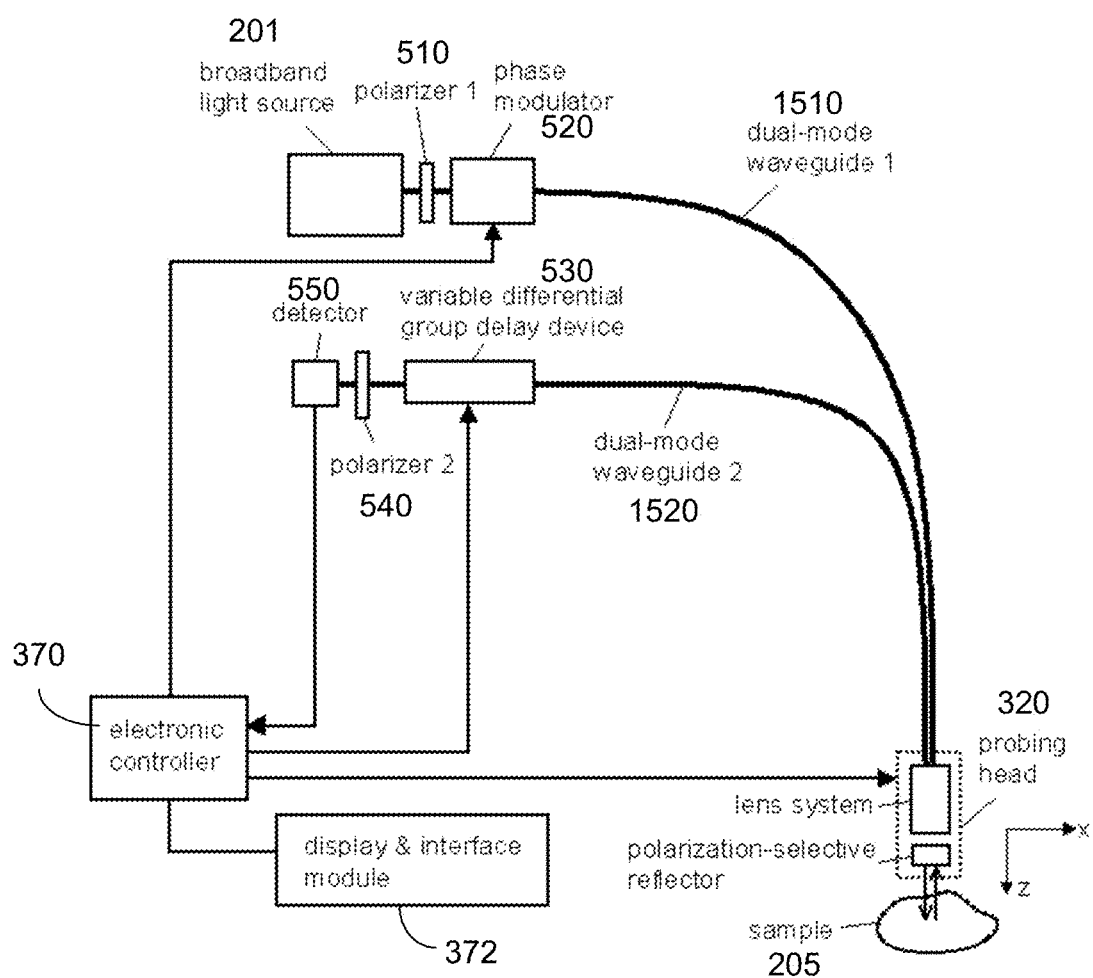
FIG. 15 illustrates an optical sensing system as an alternative to the device shown in FIG. 5B.

FIG. 15 illustrates an example for this design as an alternative to the device shown in FIG. 5B. In this design, the probing light is delivered to the sample 205 through one dual-mode waveguide 1510 and the reflected/scattered light is collected by the probe head 320 and is directed through another dual-mode waveguide 1520. With the probe head shown in FIG. 4, the mirror 424 may be oriented and aligned so that the light is reflected into the waveguide 1520 instead of the waveguide 1510. This design may be applied to other devices based on the disclosure of this application, including the exemplary devices in FIGS. 2, 3, 8A, 8B and 9.

The above-described devices and techniques may be used to obtain optical measurements of a given location of the sample at different depths by controlling the relative phase delay between two modes at different values and optical measurements of different locations of the sample to get a tomographic map of the sample at a given depth or various depths by laterally changing the relative position of the probe head over the sample. Such devices and techniques may be further used to perform other measurements on a sample, including spectral selective measurements on a layer of a sample.

In various applications, it may be beneficial to obtain information about certain substances, identifiable through their spectral absorbance, dispersed in the samples. For this purpose, a tunable bandpass filter may be used to either filter the light incident to the probe head to select a desired spectral window within the broadband spectrum of the incident light to measure the response of the sample and to vary the center wavelength of the spectral window to measure a spectral distribution of the responses of the sample. This tuning of the bandpass filter allows a variable portion of the source spectrum to pass while measuring the distribution of the complex reflection coefficient of the sample.

Alternatively, the broadband light may be sent to the optical probe head without optical filtering and the spectral components at different wavelengths in the output light from the probe head may be selected and measured to measure the response of the sample around a selected wavelength or the spectral distribution of the responses of the sample. In one implementation, a tunable optical bandpass filter may be inserted in the optical path of the output light from the probe head to filter the light. In another implementation, a grating or other diffractive optical element may be used to optically separate different spectral components in the output light to be measured by the detection subsystem or the detector.

Figure 16:
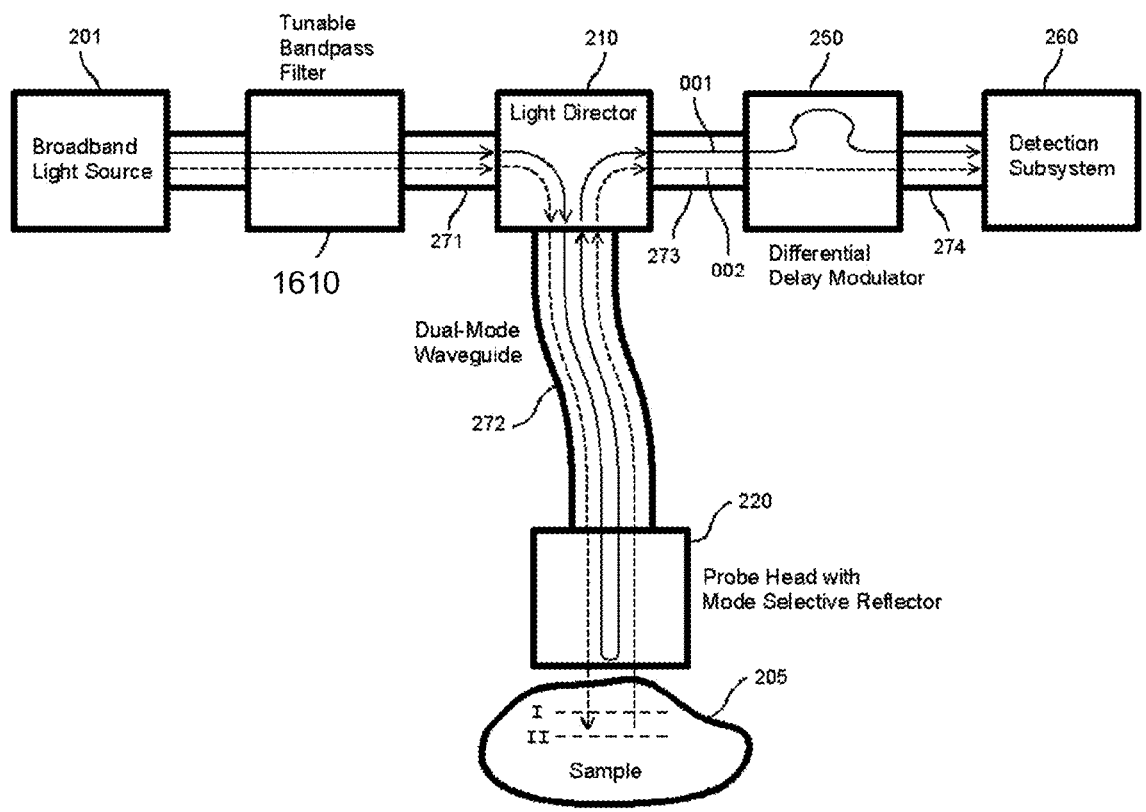
FIG. 16 shows a system based on the design in FIG. 2 where a tunable filter is inserted in the input waveguide to filter the input light in two different modes.
Figure 17:
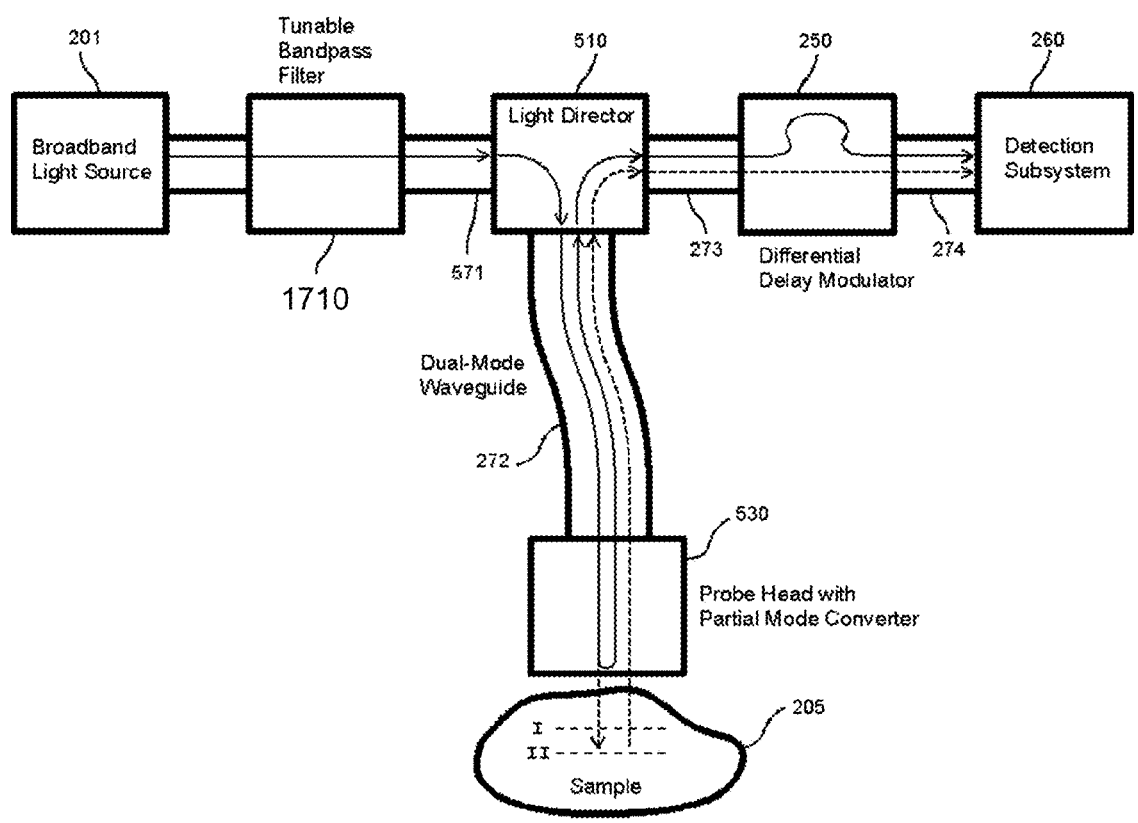
FIG. 17 shows another exemplary system based on the design in FIG. 8A where a tunable filter is inserted in the input waveguide to filter the input light in a single mode.

As an example, FIG. 16 shows a system based on the design in FIG. 2 where a tunable filter 1610 is inserted in the input waveguide 271 to filter the input light in two different modes. FIG. 17 shows another exemplary system based on the design in FIG. 8A where a tunable filter 1710 is inserted in the input waveguide 871 to filter the input light in a single mode. Such a tunable filter may be placed in other locations.

Figure 18:
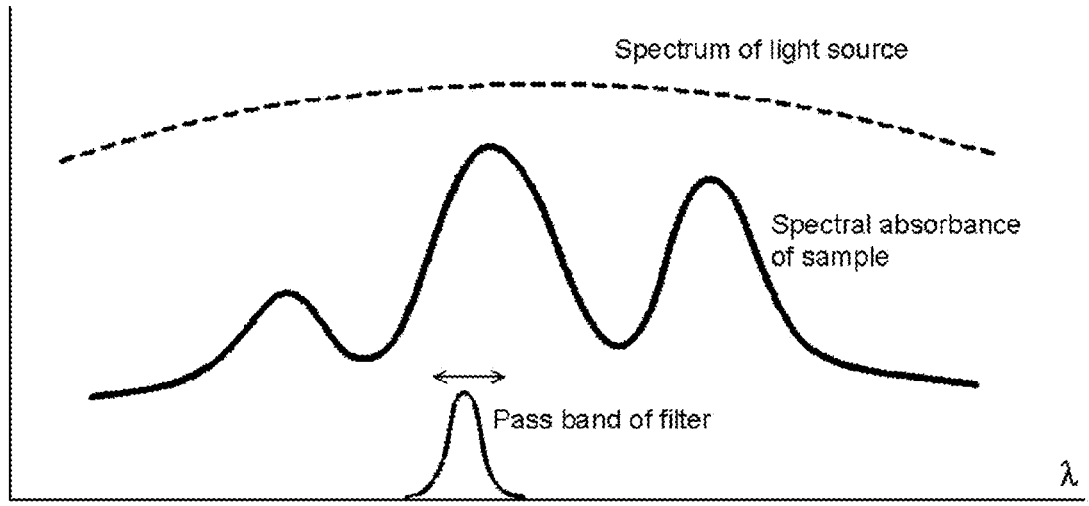
FIG. 18 illustrates the operation of the tunable bandpass filter in the devices in FIGS. 16 and 17.

FIG. 18 illustrates the operation of the tunable bandpass filter in the devices in FIGS. 16 and 17. The filter selects a narrow spectral band within the spectrum of the light source to measure the spectral feature of the sample.

Notably, the devices and techniques of this application may be used to select a layer within a sample to measure by properly processing the measured data. Referring back to the devices in FIGS. 16 and 17, let us assume that the absorption characteristics of a layer bounded by interfaces I and II is to be measured. For the simplicity of description, it is assumed that the spectral absorption of the substance in the layer is characterized by a wavelength-dependent attenuation coefficient $\mu_h(\lambda)$ and that of other volume is characterized by $\mu_g(\lambda)$. It is further assumed that the substance in the vicinity of interface I (II) possesses an effective and wavelength independent reflection coefficient $r_I$ ($r_{II}$). If the characteristic absorption of interest is covered by the spectrum of the light source, an optical filter 1610 or 1710 with a bass band tunable across the characteristic absorption of the sample 205 may be used to measure the spectral responses of the sample 205 centered at different wavelengths.

In operation, the following steps may be performed. First, the differential delay modulator 250 is adjusted so that the path length traveled by one mode (e.g., the mode 001) matches that of radiation reflected from interface I in the other mode (e.g., the mode 002). At this point, the pass band of filter 1610 or 1710 may be scanned while recording the oscillation of the measured signal due to a periodic differential phase generated by the modulator 250. The oscillation amplitude as a function of wavelength is given by $$A_I(\lambda) = r_I e^{-2\mu_g(\lambda)z_I} \tag{15}$$

where $z_I$ is the distance of interface I measured from the top surface of the sample 205. Next, the differential delay modulator 250 is adjusted again to change the differential delay so that the path length traveled by the mode 001 matches that of radiation reflected from interface II in the mode 002. The measurement for the interface II is obtained as follows:

$$A_{II}(\lambda) = r_{II} e^{-2\mu_g(\lambda)z_I - 2\mu_h(\lambda)z_{II}}, \tag{16}$$

where $z_{II}$ is the distance of interface II measured from interface I. To acquire the absorption characteristics of the layer bounded by the interfaces I and II, Eq. (7) and Eq. (6) can be used to obtain the following ratio:

$$\frac{A_{II}(\lambda)}{A_I(\lambda)} = \frac{r_{II}}{r_I} e^{-2\mu_h(\lambda)z_{II}}. \tag{17}$$

Notably, this equation provides the information on the absorption characteristics of the layer of interest only and this allows measurement on the layer. This method thus provides a "coherence gating" mechanism to optically acquire the absorbance spectrum of a particular and designated layer beneath a sample surface.

It should be noted that the pass band of the optical filter 1610 or 1710 may be designed to be sufficiently narrow to resolve the absorption characteristics of interest and at the meantime broad enough to differentiate the layer of interest. The following example for monitoring the glucose level by optically probing a patient's skin shows that this arrangement is reasonable and practical.

Various dependable glucose monitors rely on taking blood samples from diabetes patients. Repeated pricking of skin can cause considerable discomfort to patients. It is therefore desirable to monitor the glucose level in a noninvasive manner. It is well known that glucose in blood possesses "signature" optical absorption peaks in a near-infrared (NIR) wavelength range. It is also appreciated the main obstacle in noninvasive monitoring of glucose is due to the fact that a probing light beam interacts, in its path, with various types of tissues and substances which possess overlapping absorption bands. Extracting the signature glucose peaks amongst all other peaks has proven difficult.

The above "coherence gating" may be used overcome the difficulty in other methods for monitoring glucose. For glucose monitoring, the designated layer may be the dermis layer where glucose is concentrated in a network of blood vessels and interstitial fluid.

Figure 19A:
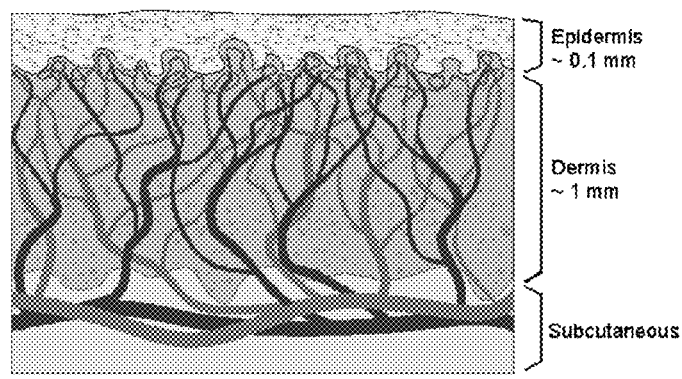
FIG. 19A illustrates an example of a human skin tissue where the optical sensing technique described here can be used to measure the glucose concentration in the dermis layer between the epidermis and the subcutaneous layers.

FIG. 19A illustrates an example of a human skin tissue where the coherence gating technique described here can be used to measure the glucose concentration in the dermis layer between the epidermis and the subcutaneous layers. The dermis layer may be optically selected and measured with the coherence gating technique. It is known that the superficial epidermis layer, owing to its pigment content, is the dominant source of NIR absorption. Because of the absence of blood, however, the epidermis yields no useful information for glucose monitoring. The coherent gating technique can be applied to acquire solely the absorbance spectrum of the dermis layer by rejecting the absorptions of the epidermis and the subcutaneous tissues. An additional advantage of this technique is from the fact that dermis exhibits less temperature variation compared to the epidermis. It is known that surface temperature variation causes shifts of water absorption, hampering glucose monitoring.

Figure 19B:
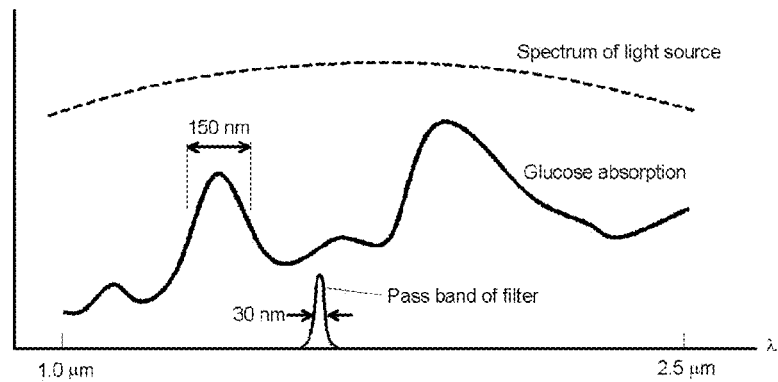
FIG. 19B shows some predominant glucose absorption peaks in blood in a wavelength range between 1 and 2.5 microns.

FIG. 19B shows some predominant glucose absorption peaks in blood in a wavelength range between 1 and 2.5 microns. The width of these peaks are approximately 150 nm. To resolve the peaks, the bandwidth of the tunable bandpass filter may be chosen to be around 30 nm. The depth resolution is determined by the following equation:

$$\frac{2\ln(2)}{\pi} \frac{\lambda_o^2}{\Delta\lambda} = 60 \ \mu m \quad (18)$$

Therefore, the coherence gating implemented with the devices in FIGS. 16 and 17 or other optical sensing devices may be used to determine the absorption characteristics of the glucose in tissue layers no less than 60 μm thick. As illustrated in FIG. 19A, human skin consists of a superficial epidermis layer that is typically 0.1 mm thick. Underneath epidermis is the dermis, approximately 1 mm thick, where glucose concentrates in blood and interstitial fluids. The above analysis indicates that it is possible to use the apparatus shown in FIGS. 16 and 17 to isolate the absorption characteristics of the dermis from that of the epidermis and other layers.

It is clear from Eq. (18) that the product of spectral resolution and layer resolution is a constant for a given center wavelength $\lambda_o$. The choice of the filter bandwidth should be made based on the tradeoff between these two resolutions against the specific requirements of the measurement.

The tunable bandpass filter 1610 or 1710 may be operated to acquire the absorption characteristics of an isolated volume inside a sample.

Figure 20:
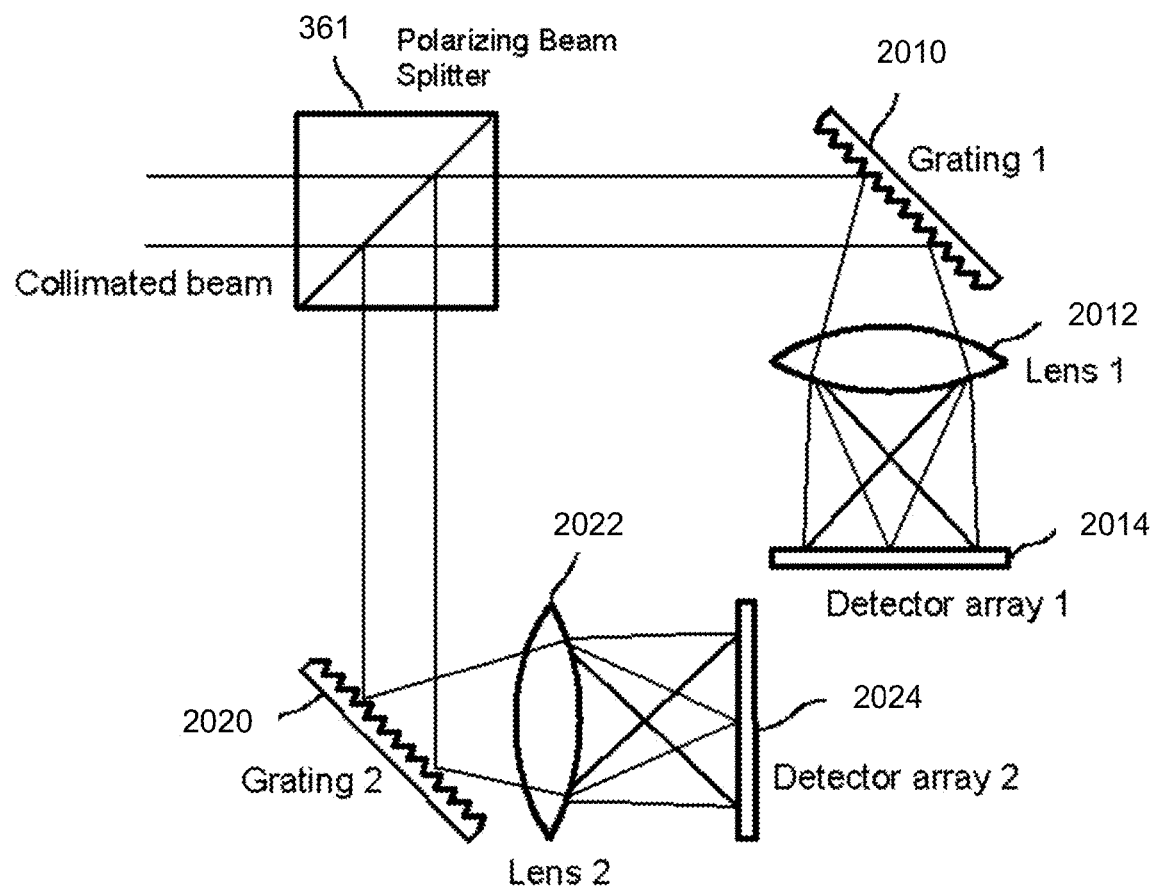
FIG. 20 illustrates one exemplary implementation of the detection subsystem in FIG. 3 where two diffraction gratings are used to separate different spectral components in the output light beams from the polarizing beam splitter.

FIG. 20 illustrates one exemplary implementation of the detection subsystem 260 in FIG. 3 where two diffraction gratings 2010 and 2020 are used to separate different spectral components in the output light beams from the polarizing beam splitter 361. A lens 2012 is positioned to collect the diffracted components from the grating 2010 and focus different spectral components to different locations on its focal plane. A detector array 2014 with multiple photodetector elements is placed at the focal plane of the lens 2012 so that different spectral components are received by different photodetector elements. A second lens 2022 and a detector array 2024 are used in the optical path of the diffracted components in a similar way. In devices shown in FIGS. 5A, 5B, 8A, and 8B where a single optical detector is used for measurements, a single grating, a lens, and a detector array may be used.

In operation, each detector element receives light in a small wavelength interval. The photocurrents from all elements in an array can be summed to form a signal which is equivalent to the signal received in each single detector without the grating shown in FIG. 3. By selectively measuring the photocurrent from an individual element or a group of elements in an array, the spectral information of the sample can be obtained.

Only a few implementations are disclosed in this application. However, it is understood that variations and enhancements may be made.

What is claimed is:

1. A method for optically measuring a sample, comprising:
directing one beam of guided light in a first propagation mode to a sample;
directing a first portion of the guided light in the first propagation mode at a location near the sample away from the sample before the first portion reaches the sample while allowing a second portion in the first propagation mode to reach the sample;
controlling a reflection of the second portion from the sample to be in a second propagation mode different from the first propagation mode to produce a reflected second portion; and
directing both the reflected first portion in the first propagation mode and the reflected second portion in the second propagation mode through a common waveguide into a detection module to extract information from the reflected second portion on the sample.

2. The method as in claim 1, wherein the first propagation mode and the second propagation mode are two polarization modes that are orthogonal to each other.

3. The method as in claim 2, wherein the first propagation mode and the second propagation mode are two orthogonal linear polarization modes.

4. The method as in claim 2, further comprising using a polarization rotator to cause the reflected second portion to be in the second propagation mode.

5. The method as in claim 2, further comprising using a Faraday rotator to cause the reflected second portion to be in the second propagation mode.

6. The method as in claim 2, further comprising using a quarter wave plate to cause the reflected second portion to be in the second propagation mode.

7. The method as in claim 1, further comprising using the common waveguide to both direct the guided light to the sample and to guide the reflected first portion and the reflected second portion away from the sample.

8. The method as in claim 7, wherein the waveguide is a polarization maintaining waveguide.

9. The method as in claim 7, wherein the waveguide is a polarization maintaining fiber.

10. The method as in claim 1, further comprising using an input waveguide different from the common waveguide to direct the guided light to the sample.

11. The method as in claim 1, further comprising adjusting a relative phase delay between the reflected first portion and the reflected second portion.

12. The method as in claim 1, further comprising:
mixing energy of the first propagation mode and the second propagation mode in the detection module to produce a first optical signal and a second optical signal; and
detecting the first and second optical signals to extract the information of the sample.

13. The method as in claim 12, further comprising using a difference between the first optical signal and the second optical signal to extract the information of the sample.

14. The method as in claim 13, further comprising:
modulating a relative phase delay between the reflected first portion and the reflected second portion at a modulation frequency; and
using information on amplitudes of the difference at the modulation frequency and a harmonic of the modulation frequency to extract the information of the sample.

15. The method as in claim 12, further comprising:
separating different optical spectral components in the first optical signal;
measuring the different optical spectral components in the first optical signal;
separating different optical spectral components in the second optical signal;
measuring the different optical spectral components in the second optical signal; and
using the measurements to obtain a spectral response of the sample at a spectral component selected from the different optical spectral components.

16. The method as in claim 15, further comprising using an optical grating to separate the different optical spectral components in the first optical signal by optical diffraction.

17. The method as in claim 1, further comprising controlling a spectral property of the guided light to the sample to obtain the information of the sample.

18. The method as in claim 1, further comprising using a tunable optical bandpass filter to select a center wavelength of a spectral range of the guided light to the sample to obtain a spectral response of the sample in the spectral range.

19. A device for optically measuring a sample, comprising:
a waveguide to receive and guide an input beam in a first propagation mode;
a probe head coupled to the waveguide to receive the input beam and to reflect a first portion of the input beam back to the waveguide in the first propagation mode and direct a second portion of the input beam to a sample, the probe head collecting reflection of the second portion from the sample and exporting to the waveguide the reflection as a reflected second portion in a second propagation mode different from the first propagation mode; and
a detection module to receive the reflected first portion and the reflected second portion in the waveguide and to extract information of the sample carried by the reflected second portion.

20. A method for optically measuring a sample, comprising:
directing light in a first propagation mode to a vicinity of a sample under measurement;
directing a first portion of the light in the first propagation mode to propagate away from the sample at the vicinity of the sample without reaching the sample;
directing a second portion of the light in the first propagation mode to the sample to cause reflection at the sample;
controlling reflected light from the sample to be in a second propagation mode that is independent from the first propagation mode to co-propagate with the first portion along a common optical path; and
using the first portion in the first propagation mode and the reflected light in the second propagation mode to obtain information of the sample.

* * * * *